US012201321B2

United States Patent
Gross et al.

(10) Patent No.: US 12,201,321 B2
(45) Date of Patent: Jan. 21, 2025

(54) ACCESS DEVICES, TREATMENT DEVICES, AND KITS USEFUL FOR PERFORMING TREATMENT UNDER MAGNETIC RESONANCE IMAGING AND RELATED METHODS

(71) Applicant: Cook Medical Technologies LLC, Bloomington, IN (US)

(72) Inventors: David Gross, Lafayette, IN (US); Neal Fearnot, West Lafayette, IN (US); Sean D. Chambers, Bloomington, IN (US); Eric Brandner, West Lafayette, IN (US); Ram H. Paul, Jr., Bloomington, IN (US); Gary L. Neff, Bloomington, IN (US); Creasy Clauser Huntsman, Lafayette, IN (US)

(73) Assignees: Cook Medical Technologies LLC, Bloomington, IN (US); Muffin Incorporated, West Lafayette, IN (US)

( * ) Notice: Subject to any disclaimer, the term of this patent is extended or adjusted under 35 U.S.C. 154(b) by 106 days.

(21) Appl. No.: 17/573,104

(22) Filed: Jan. 11, 2022

(65) Prior Publication Data

US 2022/0218392 A1 Jul. 14, 2022

Related U.S. Application Data

(60) Provisional application No. 63/135,966, filed on Jan. 11, 2021.

(51) Int. Cl.
*A61B 17/34* (2006.01)
*A61B 5/055* (2006.01)
(Continued)

(52) U.S. Cl.
CPC .......... *A61B 17/3423* (2013.01); *A61B 5/055* (2013.01); *A61B 10/04* (2013.01);
(Continued)

(58) Field of Classification Search
None
See application file for complete search history.

(56) References Cited

U.S. PATENT DOCUMENTS 9,669,240 B2 6/2017 Köhler et al.
9,687,681 B2 6/2017 Kohler et al.
(Continued)

FOREIGN PATENT DOCUMENTS

CN 106943218 A * 7/2017 ....... A61B 17/12113

OTHER PUBLICATIONS

Fichtinger, G., Krieger, A., Susil, R. C., Tanacs, A., Whitcomb, L. L., & Atalar, E. (2002). Transrectal prostate biopsy inside closed MRI scanner with remote actuation, under real-time image guidance. In MICCAI 2002: 5th International Conference Tokyo, Japan, Sep. 25-28, 2002, (pp. 91-98) (Year: 2002).*

(Continued)

*Primary Examiner* — Jason M Ip

(74) *Attorney, Agent, or Firm* — MacMillan, Sobanski & Todd, LLC

(57) ABSTRACT

Example access devices, treatment devices, and kits useful in performing treatment under magnetic resonance imaging and related methods are described. An example access device includes an elongate tubular member formed of an MRI compatible material and moveable between a first, unexpanded configuration and a second, expanded configuration. The elongate tubular member has a central lengthwise axis, a proximal end, a distal end, an axial length, and a main body that defines a circumferential wall, a lumen, a (Continued)

proximal opening, a distal opening, and a main body opening. The main body opening is arranged in a spiral relative to the lengthwise axis and extends circumferentially along the circumferential wall. The main body opening extends along the entire axial length of the elongate tubular member from the proximal end to the distal end.

18 Claims, 15 Drawing Sheets

(51) Int. Cl.
  *A61B 10/04* (2006.01)
  *A61B 17/32* (2006.01)
  *A61B 34/20* (2016.01)
  *A61B 90/00* (2016.01)
  *G01R 33/563* (2006.01)

(52) U.S. Cl.
  CPC ...... *A61B 17/320016* (2013.01); *A61B 34/20* (2016.02); *G01R 33/56375* (2013.01); *A61B 2034/2051* (2016.02); *A61B 2090/3954* (2016.02)

(56) References Cited

U.S. PATENT DOCUMENTS

| | | | |
|---|---|---|---|
| 10,010,723 B2 | 7/2018 | Koehler | |
| 2002/0151787 A1 | 10/2002 | Bjornerud et al. | |
| 2003/0100828 A1 | 5/2003 | Engelhard et al. | |
| 2004/0254445 A1 | 12/2004 | Bittner | |
| 2005/0277829 A1* | 12/2005 | Tsonton | A61B 10/02 600/423 |
| 2006/0073101 A1 | 4/2006 | Oldfield et al. | |
| 2010/0185080 A1 | 7/2010 | Myhr | |
| 2011/0098554 A1 | 4/2011 | Mardor et al. | |
| 2012/0108881 A1* | 5/2012 | Chi Sing | A61N 5/1002 600/3 |
| 2015/0011834 A1* | 1/2015 | Ayala | A61B 17/0218 29/428 |
| 2018/0140801 A1* | 5/2018 | Voss | A61M 25/0662 |

OTHER PUBLICATIONS

CN-106943218-A translation (Year: 2017).*
Google translation of CN106943218A completed May 23, 2024 (Year: 2017).*
Espacenet patent translate of CN106943218A completed May 1, 2024 (Year: 2017).*

* cited by examiner

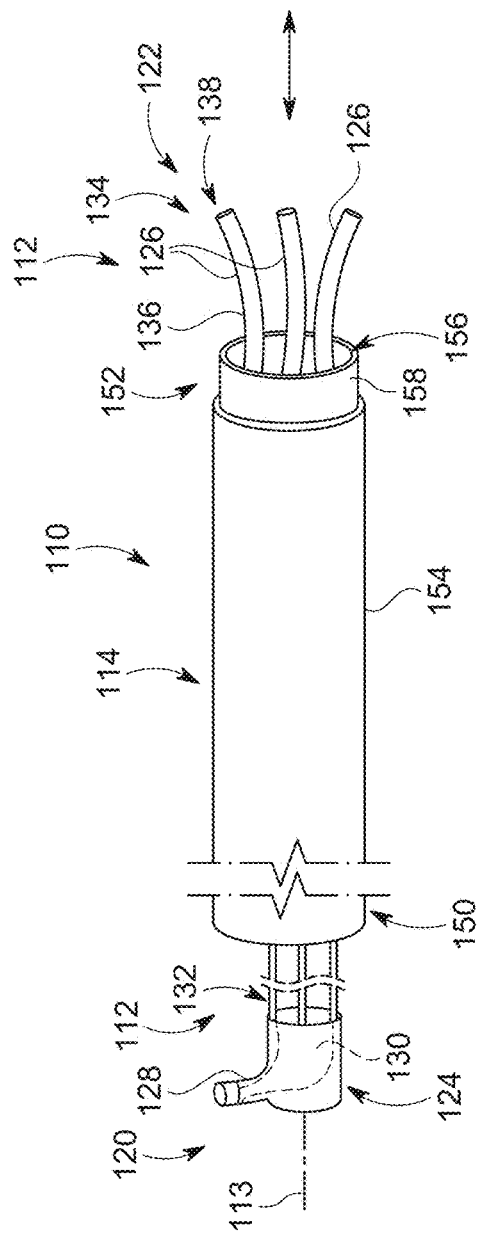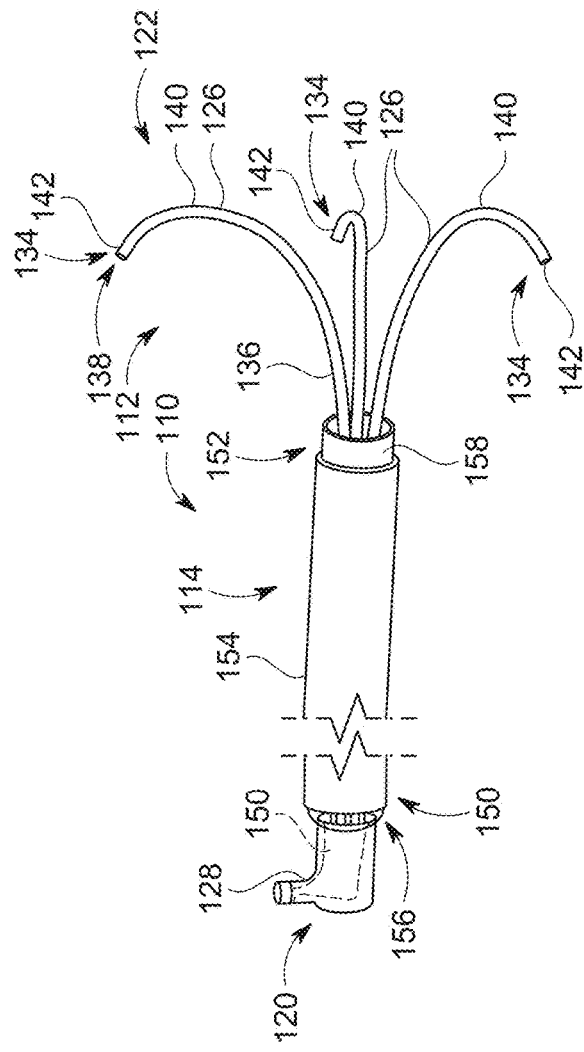

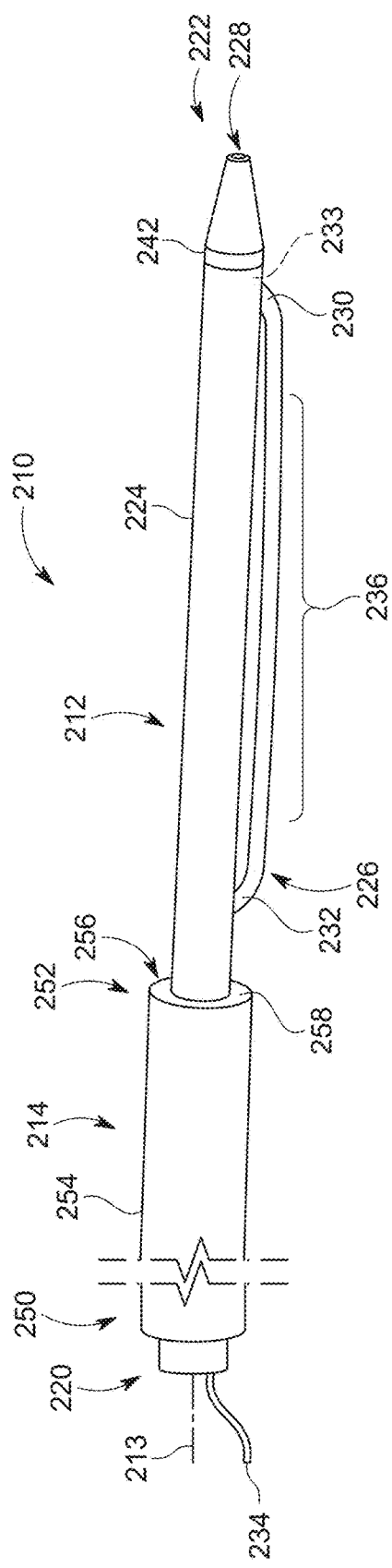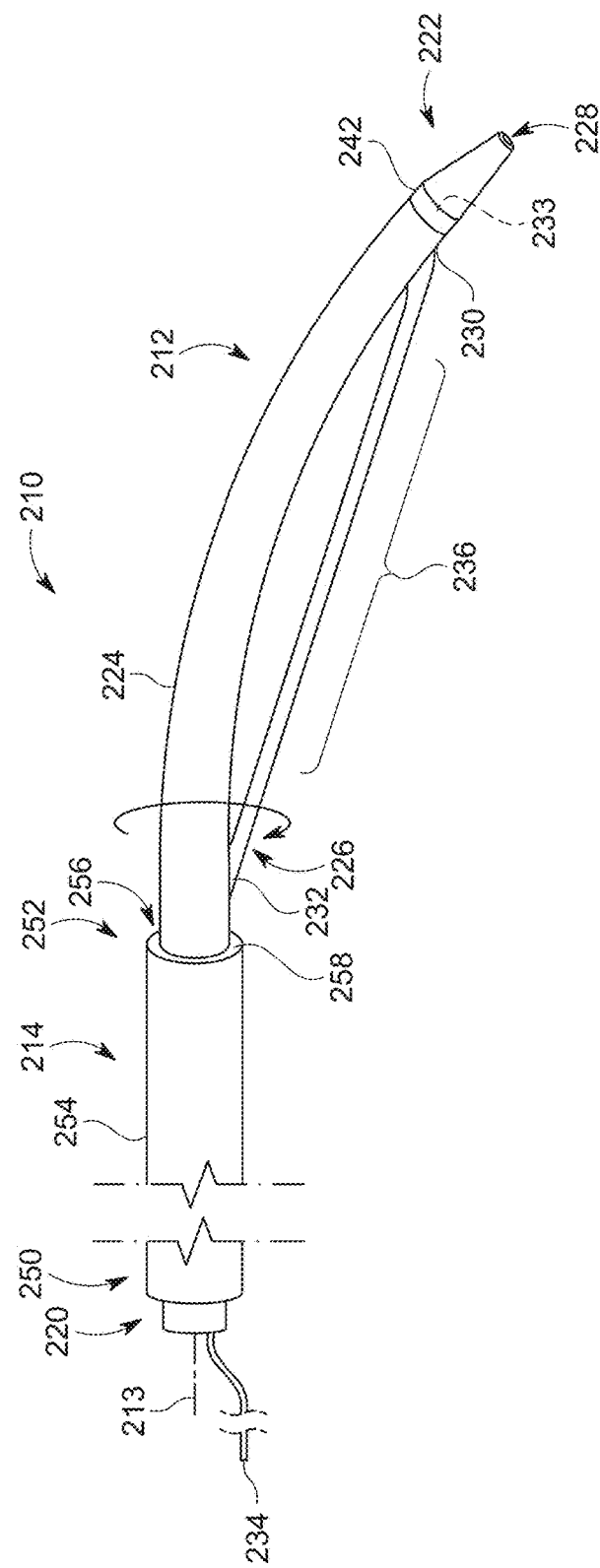
FIG. 5
FIG. 6

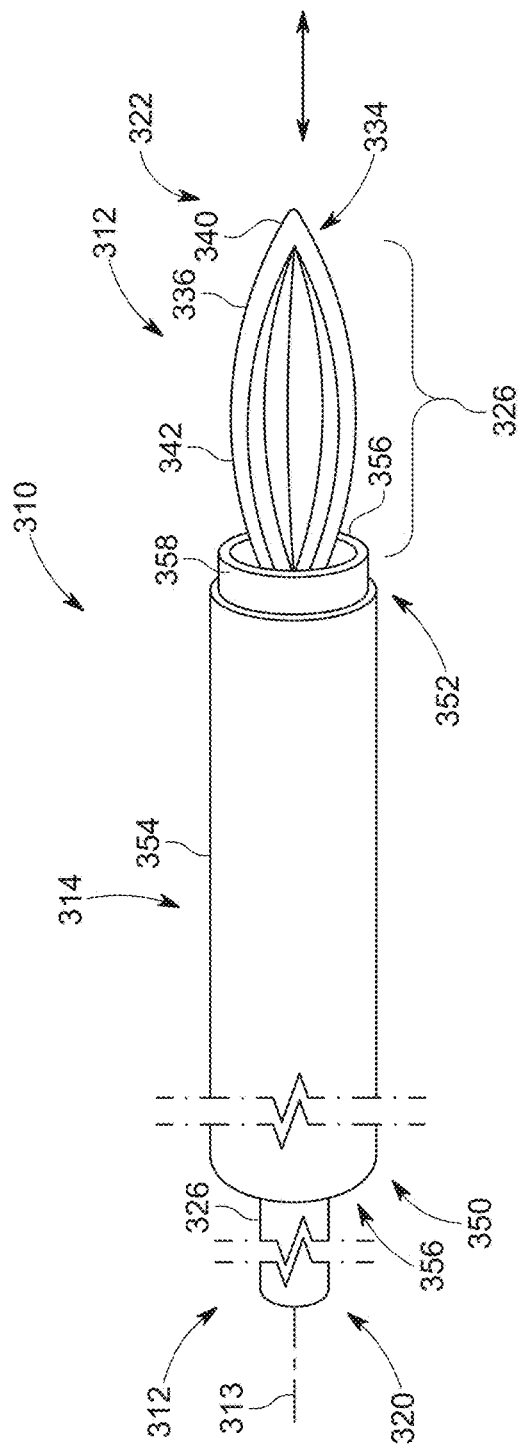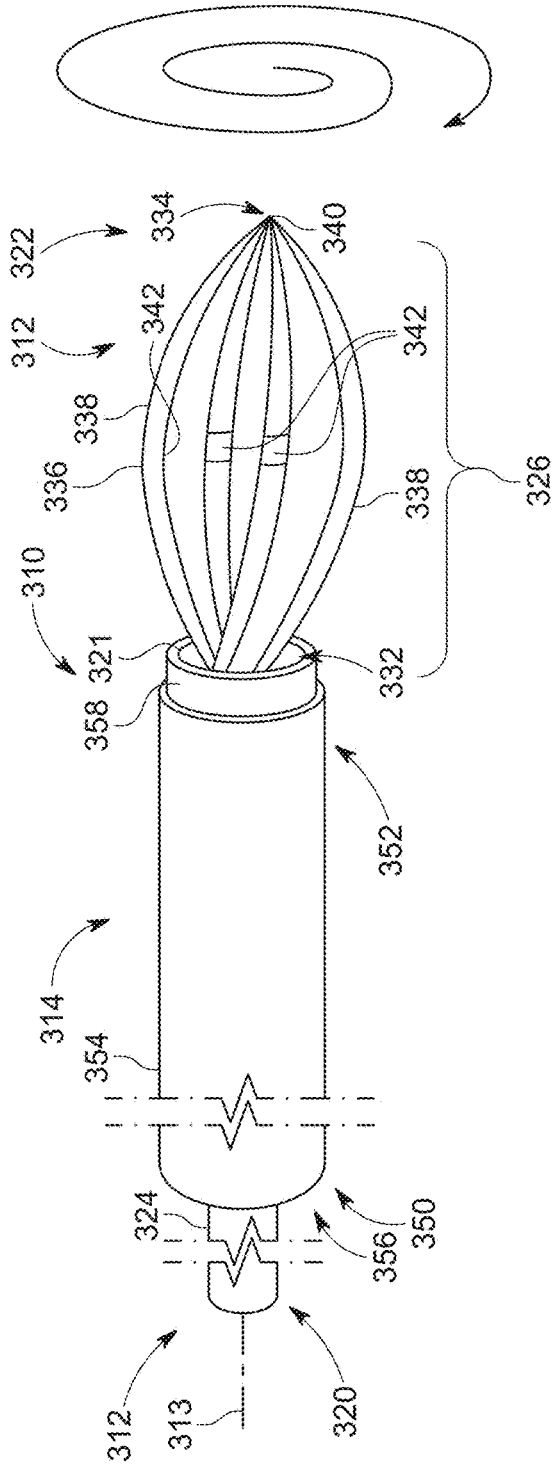
FIG. 7
FIG. 8

2.5x2.5x2.5 mm

ACCESS DEVICES, TREATMENT DEVICES, AND KITS USEFUL FOR PERFORMING TREATMENT UNDER MAGNETIC RESONANCE IMAGING AND RELATED METHODS

RELATED APPLICATIONS

This application claims priority to U.S. Provisional Application No. 63/135,966, filed Jan. 11, 2021. The entire contents of this related application are hereby incorporated by reference into this disclosure.

FIELD

The disclosure relates generally to the field of medical devices. More particularly, the disclosure relates to access devices useful in providing access to a bodily passage under magnetic resonance imaging (MRI), treatment devices useful in performing treatment under MRI, kits useful in performing treatment under MRI, and methods of performing interventional medical treatment under MRI.

BACKGROUND

The field of interventional MRI is gaining wider acceptance and seeing an increase in the number of procedures that can be performed. Interventional procedures conducted under MRI have several benefits over X-Ray-guided interventions. For example, the patient is not exposed to ionizing radiation. Also, MRI provides the ability to characterize tissue and functional flow during an interventional procedure.

The development of interventional procedures conducted under MRI has been limited as a result of the tools needed to perform these procedures being unavailable. Therefore, patients are required to make multiple visits to treatment facilities to visualize, diagnose, and treat various conditions. In addition, multiple imaging modalities are often needed, which impacts the accuracy of utilizing a magnetic resonance image in directing intervention. For example, when addressing prostate cancer, visualization, biopsy, and treatment are currently completed over the course of three patient visits. At a first visit, a scan is completed using a magnetic resonance scanner to produce an image showing the prostate and any abnormalities. The patient then leaves the facility and awaits a review of the image. If abnormalities exist, a second patient visit will occur such that a biopsy sample of the abnormal tissue can be completed. Currently, software is used to fuse the magnetic resonance image with the procedural ultrasound to provide guidance in conducting the biopsy. This fusion decreases the value of the diagnostic magnetic resonance image. The patient then leaves the facility again and awaits a review of the biopsy sample to determine whether further treatment is required (e.g., if the review results in a positive prostate cancer diagnosis). If further treatment is required, the patient will visit the facility a third time such that treatment can be performed. Completion of these three patient visits can take months, prevents the patient from receiving rapid treatment, and increases the overall costs associated with treatment. Furthermore, software used to fuse magnetic resonance images with other images (e.g., those obtained via ultrasound) have drawbacks, such as potential image overlay issues and the potential for compression shifting of tissues (e.g., prostate).

A need exists, therefore, for new and improved access devices useful in providing access to a bodily passage under MRI, treatment devices useful in performing treatment under MRI, kits useful in performing treatment under MRI, and methods of performing interventional medical treatment under MRI.

SUMMARY OF SELECTED EXAMPLE EMBODIMENTS

Various example access devices useful in providing access to a bodily passage under MRI, treatment devices useful in performing treatment under MRI, kits useful in performing treatment under MRI, and methods of performing interventional medical treatment under MRI are described herein.

An example access device useful in providing access to a bodily under MRI includes an elongate tubular member moveable between a first, unexpanded configuration and a second, expanded configuration. The elongate tubular member has a central lengthwise axis, a proximal end, a distal end, an axial length, and a main body that defines a circumferential wall, a lumen, a proximal opening, a distal opening, and a main body opening. The main body opening is arranged in a spiral relative to the lengthwise axis and extends circumferentially along the circumferential wall. The main body opening extends along the entire axial length of the elongate tubular member from the proximal end to the distal end.

An example treatment device useful in performing treatment under MRI comprises an elongate member and a tubular member partially disposed over the elongate member. The elongate member is moveable between a first, unexpanded configuration and a second, expanded configuration. The elongate member has a lengthwise axis, a proximal end, a distal end, an adaptor, and a plurality of tubular members attached to the adaptor. The adaptor is disposed on the proximal end of the elongate member, has a port, and defines a lumen. Each tubular member of the plurality of tubular members has a tubular member proximal end, a tubular member distal end, and a tubular member main body that defines a tubular member lumen and a predefined curve.

An example method of performing an interventional medical treatment under MRI comprises positioning a patient within a magnetic resonance scanner; scanning a first portion of the patient using the magnetic resonance scanner; obtaining a magnetic resonance image of the first portion of the patient; identifying a tissue that has predefined characteristics using the magnetic resonance image; while the patient remains positioned within the magnetic resonance scanner used to scan a portion of the patient, advancing a medical device into a bodily passage and to the tissue while scanning a second portion of the patient that includes the medical device using the magnetic resonance scanner; obtaining a magnetic resonance image of the second portion of the patient that includes the medical device; confirming the position of the medical device within the bodily passage; advancing a biopsy device through the medical device and to the tissue while scanning a third portion of the patient that includes the biopsy device using the magnetic resonance scanner; obtaining a magnetic resonance image of the third portion of the patient that includes the biopsy device; confirming the position of the biopsy device; collecting a tissue sample from the tissue using the biopsy device while scanning a fourth portion of the patient that includes the biopsy device and the tissue using the magnetic resonance scanner; obtaining a magnetic resonance image of the fourth portion of the patient that includes the biopsy device; confirming the tissue sample has been collected; withdrawing the biopsy device and the tissue sample through the medical device; determining whether the tissue sample meets a predefined criterion; if the tissue sample meets the predefined criterion, advancing an anchor member through the medical device through which the biopsy device was advanced and to the tissue while the patient remains positioned within the magnetic resonance scanner; securing the anchor member to the tissue so that the anchor member is attached to the tissue to retain the position of the medical device relative to the tissue; advancing an access device over the medical device and toward the tissue; removing the anchor member from the tissue so that the anchor member is not attached to the tissue; withdrawing the anchor member from the bodily passage; withdrawing the medical device from the bodily passage; advancing a treatment device through the access device and to the tissue; manipulating the tissue using the treatment device; withdrawing the treatment device from the access device; withdrawing the access device from the bodily passage.

Another example method of performing an interventional medical treatment under MRI comprises positioning a patient within a magnetic resonance scanner; scanning a first portion of the patient using the magnetic resonance scanner; obtaining a magnetic resonance image of the first portion of the patient; identifying a tissue that has predefined characteristics using the magnetic resonance image; while the patient remains positioned within the magnetic resonance scanner used to scan a portion of the patient, advancing a medical device into a bodily passage and to the tissue while scanning a second portion of the patient that includes the medical device using the magnetic resonance scanner; obtaining a magnetic resonance image of the second portion of the patient that includes the medical device; confirming the position of the medical device within the bodily passage; advancing an anchor member through the medical device and to the tissue while the patient remains positioned within the magnetic resonance scanner; securing the anchor member to the tissue so that the anchor member is attached to the tissue; withdrawing the medical device from the bodily passage; advancing an access device over the anchor member and toward the tissue; removing the anchor member from the tissue; withdrawing the anchor member from the bodily passage; advancing a biopsy device through the access device and to the tissue while scanning a third portion of the patient that includes the biopsy device using the magnetic resonance scanner; obtaining a magnetic resonance image of the third portion of the patient that includes the biopsy device; confirming the position of the biopsy device; collecting a tissue sample from the tissue using the biopsy device while scanning a fourth portion of the patient that includes the biopsy device and the tissue using the magnetic resonance scanner; obtaining a magnetic resonance image of the fourth portion of the patient that includes the biopsy device; confirming the tissue sample has been collected; withdrawing the biopsy device and the tissue sample through the access device; determining whether the tissue sample meets a predefined criterion; if the tissue sample meets the predefined criterion, advancing a treatment device through the access device and to the tissue; manipulating the tissue using the treatment device; withdrawing the treatment device from the access device; withdrawing the access device from the bodily passage; removing the patient from the magnetic resonance scanner.

An example method of performing treatment on a prostate under MRI comprises positioning a patient within a magnetic resonance scanner; scanning a prostate and surrounding tissue of the patient using the magnetic resonance scanner; obtaining a magnetic resonance image of the prostate and surrounding tissue of the patient; identifying a tissue within the magnetic resonance image that has predefined characteristics; while the patient remains positioned within the magnetic resonance scanner used to scan the prostate and surrounding tissue, advancing a medical device into a bodily passage and to the tissue while scanning a first portion of the patient that includes the medical device using the magnetic resonance scanner; obtaining a magnetic resonance image of the second portion of the patient that includes the medical device; confirming the position of the medical device within the bodily passage; advancing a biopsy device through the medical device and to the tissue while scanning a third portion of the patient that includes the biopsy device using the magnetic resonance scanner; obtaining a magnetic resonance image of the third portion of the patient that includes the biopsy device; confirming the position of the biopsy device; collecting a tissue sample from the tissue using the biopsy device while scanning a fourth portion of the patient that includes the biopsy device and the tissue using the magnetic resonance scanner; obtaining a magnetic resonance image of the fourth portion of the patient that includes the biopsy device; confirming the tissue sample has been collected; withdrawing the biopsy device and the tissue sample through the medical device; determining whether the tissue sample meets a predefined criterion; if the tissue sample meets the predefined criterion, advancing an anchor member through the medical device through which the biopsy device was advanced and to the tissue while the patient remains positioned within the magnetic resonance scanner; securing the anchor member to the tissue so that the anchor member is attached to the tissue to retain the position of the medical device relative to the tissue; advancing an access device over the medical device and toward the tissue; removing the anchor member from the tissue; withdrawing the anchor member from the bodily passage; withdrawing the medical device from the bodily passage; advancing a treatment device through the access device and to the tissue; manipulating the tissue using the treatment device; withdrawing the treatment device from the access device; withdrawing the access device from the bodily passage.

An example kit useful in performing treatment under MRI includes an access device and a plurality of treatment devices according to embodiments.

Additional understanding of these example access devices, treatment devices, kits, and methods can be obtained by review of the detailed description, below, and the appended drawings.

BRIEF DESCRIPTION OF THE DRAWINGS

FIG. 3 is a partial perspective view of a first example treatment device. The treatment device is shown in a first, unexpanded configuration.

FIG. 4 is another partial perspective view of the treatment device illustrated in FIG. 3. The treatment device is shown in a second, expanded configuration.

FIG. 5 is a partial perspective view of a second example treatment device. The elongate member of the treatment device is shown in a first, substantially straight configuration.

FIG. 6 is another partial perspective view of the treatment device illustrated in FIG. 5. The elongate member of the treatment device is shown in a second, curved configuration.

FIG. 7 is a partial perspective view of a third example treatment device. The elongate member of the treatment device is shown in a first, substantially straight configuration.

FIG. 8 is another partial perspective view of the treatment device illustrated in FIG. 7. The elongate member of the treatment device is shown in a second, curved configuration.

DETAILED DESCRIPTION OF SELECTED EXAMPLES

The following detailed description and the appended drawings describe and illustrate various example access devices useful in performing treatment under MRI, treatment devices useful in performing treatment under MRI, kits useful in performing treatment under MRI, and methods of performing interventional medical treatment under MRI. The description and illustration of these examples are provided to enable one skilled in the art to make and use an access device, a treatment device, a kit, and to practice a method of performing an interventional medical treatment under MRI. They are not intended to limit the scope of the invention, or the protection sought, in any manner. The invention is capable of being practiced or carried out in various ways and the examples described and illustrated herein are merely selected examples of the various ways of practicing or carrying out the invention and are not considered exhaustive.

As used herein, the term "attached" refers to one member being secured to another member such that the members do not completely separate from each other during use performed in accordance with the intended use of an item that includes the members in their attached form.

As used herein, the term "circumference" refers an external enclosing boundary of a body, element, or feature and does not impart any structural configuration on the body, element, or feature.

Figure 1:
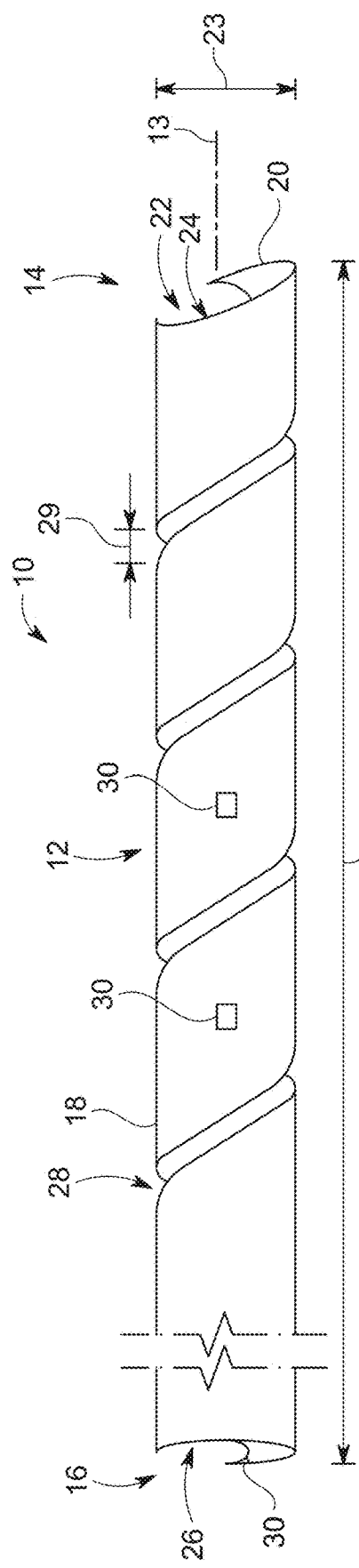
FIG. 1 is a partial perspective view of a first example access device. The access device is shown in a first, unexpanded configuration.
Figure 2:
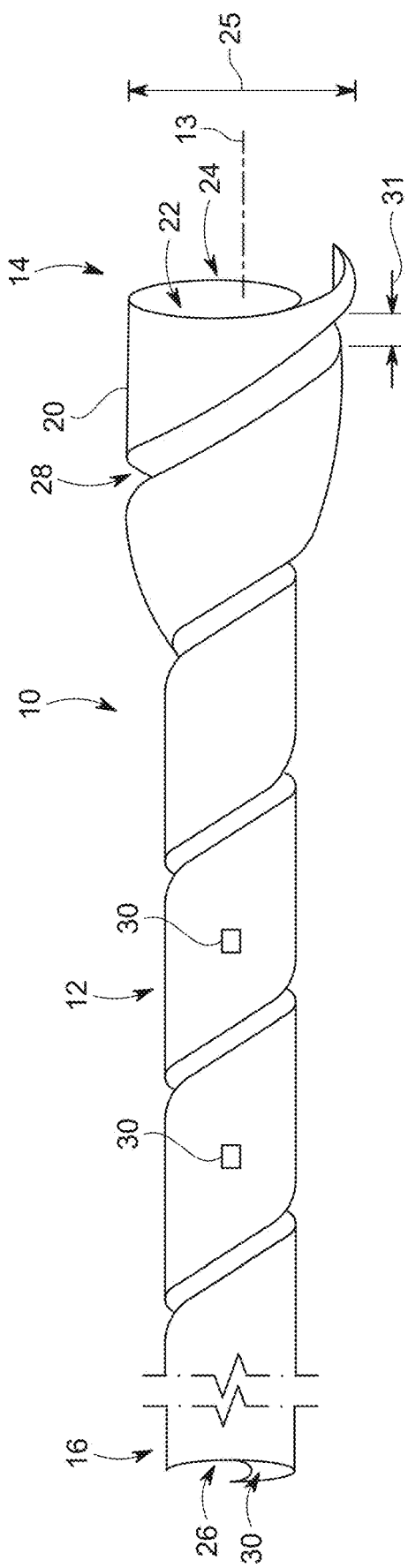
FIG. 2 is another partial perspective view of the access device illustrated in FIG. 1. The access device is shown in a second, expanded configuration.

FIG. 1 illustrates a first example access device 10. In this example, the access device 10 is an elongate tubular member 12 that is moveable between a first, unexpanded configuration, as shown in FIG. 1, and a second, expanded configuration, as shown in FIG. 2, as one or more devices are passed through the elongate tubular member 12.

The elongate tubular member 12 has a central lengthwise axis 13, a proximal end 14, a distal end 16, an axial length 17, and a main body 18 that defines a circumferential wall 20, a lumen 22, a proximal opening 24, a distal opening 26, and a main body opening 28. The axial length 17 extends from the proximal end 14 to the distal end 16. The circumferential wall 20 extends from the proximal end 14 to the distal end 16. Each of the proximal opening 24 and the distal opening 26 provides access to the lumen 22.

The main body opening 28 extends along the entire axial length 17 of the elongate tubular member 12 from the proximal end 14 to the distal end 16. However, in alternative embodiments, a main body opening can extend along a portion of the axial length of an elongate tubular member (e.g., between the proximal end and the distal end). The main body opening 28 is arranged in a spiral relative to the lengthwise axis 13 and extends circumferentially along the circumferential wall 20. The main body opening 28 comprises a slit that extends through the entire wall thickness of the circumferential wall 20 to provide access to the lumen 22.

The elongate tubular member 12 is moveable between the first, unexpanded configuration in which the lumen 22 has a first inside diameter 23, and the second, expanded configuration in which the lumen 22 has a second inside diameter 25 that is greater than the first inside diameter 23. Movement of the elongate tubular member 12 from the first, unexpanded configuration to the second, expanded configuration can be accomplished by passing a device through the lumen 22 that has an outside diameter that is greater than the first inside diameter 23 of the lumen 22. Movement of the elongate tubular member 12 from the second, expanded configuration to the first, unexpanded configuration can be accomplished by removing a device that has an outside diameter that is greater than the first inside diameter 23 of the lumen 22 that is disposed within the lumen 22. In the first, unexpanded configuration, the main body opening 28 has a first width 29 and in the second, expanded configuration the main body opening 28 has a second width 31 that is greater than the first width. The structural arrangement of the access device 10 is considered advantageous at least because it can be introduced into a bodily passage and expanded after the treatment site has been reached, reducing potential trauma at the treatment site.

While a single main body opening 28 has been illustrated, a main body opening included on an elongate tubular member can comprise any suitable number of openings, formed in any suitable manner, and positioned at any suitable location on an elongate tubular member. For example, a main body opening can comprise a plurality of openings arranged in any suitable configuration (e.g., an interrupted spiral) that extends circumferentially along a circumferential wall of an elongate tubular member. Each opening of the plurality of openings can comprise an elongate slit that extends through the entire wall thickness of a circumferential wall to provide access to a lumen of an elongate tubular member. Examples of methods and techniques of forming a main body opening in an elongate tubular member include laser cutting, stamping, die cutting, and any other method or technique considered suitable for a particular embodiment.

Optionally, an elastic polymeric sleeve or jacket can be positioned on an outer surface of the elongate tubular member that is moveable with the elongate tubular member between a first, unexpanded configuration and a second, expanded configuration. The polymeric sleeve can extend the along the entire axial length of the elongate tubular member, or along a portion of the axial length of the elongate tubular member. The polymeric sleeve can be reinforced by including polymeric fibers embedded or woven into the sleeve. Optionally the polymeric sleeve can be coated with a lubricious agent to reduce friction during use, as described herein. The polymeric sleeve can be applied to the outer surface of the elongate tubular member using any suitable method or technique and selection of a suitable method or technique can be based on various considerations, including the intended use of the elongate tubular member. Examples of methods and techniques considered suitable to apply a polymeric sleeve to an elongate tubular member include dipping an elongate tubular member in a solvated polymer solution, thermal bonding, extruding a tube over an elongate tubular member, and any other method or technique considered suitable for a particular embodiment. When an extruded tube is included on an elongate tubular member, the extruded tube can optionally be profiled using heat shrink polymer. The heat shrink polymer tubing can then be removed leaving a thin coating of polymer over the elongate tubular member.

In the illustrated embodiment, the elongate tubular member 12 can be formed of any suitable MRI compatible material and can include any suitable type and/or number of markers. In the illustrated embodiment, the elongate tubular member 12 is formed of an MRI compatible metal and has a plurality of passive markers 30 disposed along the axial length 17 of the elongate tubular member 12 and at the distal end 16 that allow for visualization of the elongate tubular member 12 in a magnetic resonance image and for device conspicuity without obscuring target tissue during treatment (e.g., biopsy, removal). In an alternative embodiment, an elongate tubular member can be formed of a shape memory material (e.g., Nitinol) such that it expands upon removal from a restraining tube allowing it to move from a first, unexpanded configuration to a second, expanded configuration due to being biased to the second, expanded configuration or such that it can be moved to the second, expanded configuration using a balloon. Markers of the plurality of passive markers 30 are advantageously formed of a magnetically susceptible material, such as a paramagnetic material or a ferromagnetic material.

FIGS. 3 and 4 illustrate a first example treatment device 110. In this example, the treatment device 110 is an elongate member 112 partially disposed within a tubular member 114. The elongate member 112 is moveable between a first, unexpanded configuration, as shown in FIG. 3, and a second, expanded configuration, as shown in FIG. 4.

In the illustrated embodiment, the elongate member 112 has a lengthwise axis 113, a proximal end 120, a distal end 122, an adaptor 124, and a plurality of tubular members 126 attached to the adaptor 124. The adaptor 124 (e.g., luer fitting) is disposed on the proximal end 120 of the elongate member 112, has a port 128, and defines a lumen 130. The lumen 130 is in fluid communication with the port 128 and a lumen 138 of each tubular member of the plurality of tubular members 126, as described in more detail herein.

Each tubular member of the plurality of tubular members 126 has a proximal end 132, a distal end 134, and a main body 136 that defines a lumen 138 and a predefined curve 140. In the illustrated embodiment, the plurality of tubular members 126 are arranged circumferentially about the lengthwise axis 113. However, alternative embodiments can include a plurality of tubular members that are positioned in any suitable configuration. Each tubular member of the plurality of tubular members 126 defines the predefined curve 140 when no outside forces are applied on the main body 136. Each tubular member of the plurality of tubular members 126 is moveable between a substantially straight configuration when the elongate member is in the first, unexpanded configuration, as shown in FIG. 3, and a curved configuration when the elongate member is in second, expanded configuration, as shown in FIG. 4. The lumen 138 extends from the proximal end 132 to the distal end 134 and is in fluid communication with the lumen 130 defined by the adaptor 124. In the illustrated embodiment, the plurality of tubular members 126 is formed of a shape memory alloy (e.g., Nitinol) and each tubular member of the plurality of tubular members 126 includes a passive marker 142 on its distal end 134 that allows for visualization of the tubular members 126 in a magnetic resonance image and for device conspicuity without obscuring target tissue during treatment (e.g., biopsy, removal). In an alternative embodiment, a plurality of tubular member can be short relative to the length of the elongate member and be connected at the proximal end to a semi-rigid tube for column strength.

The tubular member 114 is disposed over the elongate member 112 and has a proximal end 150, a distal end 152, and a main body 154 that defines a lumen 156. The lumen 156 extends from the proximal end 150 to the distal end 152 and is sized to receive the elongate member 112. In the illustrated embodiment, the tubular member 114 includes a passive marker 158 on its distal end 152 that allows for visualization of the tubular member 114 in a magnetic resonance image and for device conspicuity without obscuring target tissue during treatment (e.g., biopsy, removal).

In the first, unexpanded configuration, the distal end 122 of the elongate member 112 is disposed within the lumen 156 defined by the tubular member 114. To move the elongate member 112 from the first, unexpanded configuration to the second, expanded configuration a distally-directed force is applied on the elongate member 112 while maintaining the position of the tubular member 114 such that the elongate member 112 is advanced out of the tubular member 114. Alternatively, the position of the elongate member 112 can be maintained while applying a proximally-directed force on the tubular member 114, or a distally-directed force can be applied on the elongate member 112 while applying a proximally-directed force on the tubular member 114. This results in the distal end 122 of the elongate member 112 being advanced out of the tubular member 114 and each tubular member of the plurality of tubular members 126 defining the predefined curve 140. Force can be applied on the elongate member 112 and/or tubular member 114, as described above, until a desired amount of the plurality of tubular members 126 is advanced out of the tubular member 114. Subsequently, a fluid can be passed through the port 128 of the adaptor 124 and through the lumen 138 of each tubular member of the plurality of tubular member 126 to treat tissue. Examples of fluids considered suitable to pass through a tubular member include chemicals, chemotherapeutic agents, cryo-ablatives, ablative therapies, and any other fluid considered suitable for a particular embodiment. The treatment device 110 is considered advantageous at least because it provides a mechanism for injecting a fluid into a larger area of tissue relative to a single needle and because it can be positioned and deployed to a desired diameter within the tissue.

Once a desired treatment has been accomplished, the elongate member 112 can be moved from the second, expanded configuration to the first, unexpanded configuration. This can be accomplished by applying a proximally-directed force on the elongate member 112 while maintaining the position of the tubular member 114 such that the elongate member 112 is advanced into the lumen 156 of the tubular member 112. Alternatively, the position of the elongate member 112 can be maintained while applying a distally-directed force on the tubular member 114, or a proximally-directed force can be applied on the elongate member 112 while applying a distally-directed force on the tubular member 114. This results in the distal end 122 of the elongate member 112 being advanced into the lumen 156 of the tubular member 114 and each tubular member of the plurality of tubular members 126 defining a substantially straight configuration within the lumen 156 of the tubular member 114. Force is applied on the elongate member 112 and/or tubular member 114, as described above, until a desired amount of the plurality of tubular members 126 is advanced into the lumen 156 of the tubular member 114.

FIGS. 5 and 6 illustrate a second example treatment device 210. In this example, the treatment device 210 is an elongate member 212 partially disposed within a tubular member 214. The elongate member 212 is moveable between a first, substantially straight configuration, as shown in FIG. 5, and a second, curved configuration, as shown in FIG. 6.

In the illustrated embodiment, the elongate member 212 has a lengthwise axis 213, a proximal end 220, a distal end 222, a main body 224, and a cutting member 226. The main body 224 defines a lumen 228, a first opening 230, and a second opening 232. The lumen 228 extends from the proximal end 220 to the distal end 222. Each of the first opening 230 and the second opening 232 extends through the main body 224 and is in fluid communication with the lumen 228. The first opening 230 is disposed between the second opening 232 and the distal end 222 and the second opening 232 is disposed between the first opening 230 and the proximal end 220.

The cutting member 226 has a first end 233, a second end 234, a length that extends from the first end 233 to the second end 234, and a cutting blade 236. The first end 233 is attached to the distal end 222 of the elongate member 212 within the lumen 226. The cutting member 226 extends from the first end 233, through the first opening 230, along an exterior surface of the elongate member 212, through the second opening 232 and into the lumen 226, through the lumen 226 defined by the elongate member 212 to the second end 234. The cutting blade 236 is disposed between the first and second openings 230, 232 defined by the elongate member 212. The cutting member 226 is moveable between a first position, as shown in FIG. 5, and a second position, as shown in FIG. 6. The elongate member 212 is in the first, substantially straight configuration when the cutting member 226 is in the first position and the elongate member 212 is in the second, curved configuration when the cutting member 226 is in the second position. In the illustrated embodiment, the elongate member 212 includes a passive marker 242 between its proximal end 220 and its distal end 222 that allows for visualization of the elongate member 212 in a magnetic resonance image and for device conspicuity without obscuring target tissue during treatment (e.g., biopsy, removal).

The tubular member 214 is disposed over the elongate member 212 and has a proximal end 250, a distal end 252, and a main body 254 that defines a lumen 256. The lumen 256 extends from the proximal end 250 to the distal end 252 and is sized to receive the elongate member 212. In the illustrated embodiment, the tubular member 214 includes a passive marker 258 on its distal end 252 that allows for visualization of the tubular member 214 in a magnetic resonance image and for device conspicuity without obscuring target tissue during treatment (e.g., biopsy, removal).

The elongate member 212 can be advanced out of the lumen 256 defined by the tubular member 214 by applying a distally-directed force on the elongate member 212 while maintaining the position of the tubular member 214, applying a distally-directed force on the elongate member 212 while applying a proximally-directed force on the tubular member 214, or maintaining the position of the elongate member 212 while applying a proximally-directed force on the tubular member 214. The elongate member 212 can be advanced into the lumen 256 defined by the tubular member 214 by applying a proximally-directed force on the elongate member 212 while maintaining the position of the tubular member 214, applying a proximally-directed force on the elongate member 212 while applying a distally-directed force on the tubular member 214, or maintaining the position of the elongate member 212 while applying a distally-directed force on the tubular member 214.

To move the elongate member 212 from the first, substantially straight configuration to the second, curved configuration, tension is applied on the portion of the cutting member 226 that extends from the proximal end 220 of the elongate member 212 (e.g., first end 234) in a distal direction while maintaining the position of the elongate member 212 or applying a distally-directed force on the elongate member 212. Subsequently, torque can be applied on the elongate member 212 such that it rotates relative to tissue being treated and the cutting blade 236 cuts the tissue. Optionally, an elongate member can include a spool with a unidirectional locking gear on the proximal end of the elongate member that can apply tension, maintain tension, or remove tension from a cutting member during use. To move the elongate member 212 from the second, curved configuration to the first, substantially straight configuration, the tension is released from the cutting member 226 while maintaining the position of the elongate member 212 or a proximally-directed force is applied on the elongate member 212.

FIGS. 7 and 8 illustrate a third example treatment device 310. In this example, the treatment device 310 is an elongate member 312 partially disposed within a tubular member 314. The elongate member 312 is moveable between a first, unexpanded configuration, as shown in FIG. 7, and a second, expanded configuration, as shown in FIG. 8.

In the illustrated embodiment, the elongate member 312 has a lengthwise axis 313, a proximal end 320, a distal end 322, a main body 324, and a plurality of cutting members 326 attached to the main body 324. The main body 324 extends from the proximal end 320 to a location 321 disposed between the proximal end 320 and the distal end 322. The plurality of cutting members 326 extends from the location 321 disposed between the proximal end 320 and the distal end 322 to the distal end 322. Optionally, laser cut patterns (e.g., interlocking sections, non-elongating spiralcut sections) can be introduced into portions of the main body 324 to increase flexibility.

Each cutting member of the plurality of cutting members 326 has a proximal end 332, a distal end 334, and a main body 336 that defines a predefined curve 338 when free of outside forces. Each cutting member of the plurality of cutting member 326 has a first, substantially straight configuration when disposed within the tubular member 314 and a second, curved configuration when free of the tubular member 314. In the illustrated embodiment, the plurality of cutting members 326 are arranged circumferentially around the lengthwise axis 313. However, alternative embodiments can include a plurality of cutting members that are positioned in any suitable configuration. Each cutting member of the plurality of cutting members 326 is moveable between a substantially straight configuration when the elongate member 312 is in the first, unexpanded configuration, as shown in FIG. 7, and a curved configuration when the elongate member 312 is in the second, expanded configuration, as shown in FIG. 8. In the illustrated embodiment, each cutting member of the plurality of cutting members 326 is formed of a shape memory alloy (e.g., Nitinol, 316 Stainless Steel, MP35N, thermoplastic), the elongate member 312 includes a passive marker 340 on its distal end 322, and each cutting member of the plurality of cutting members 326 includes a passive marker 342 between the proximal end 332 and the distal end 334. The markers 340, 342 allowing for visualization of the elongate member 212 in a magnetic resonance image and for device conspicuity without obscuring target tissue during treatment (e.g., biopsy, removal).

The tubular member 314 is disposed over the elongate member 312 and has a proximal end 350, a distal end 352, and a main body 354 that defines a lumen 356. The lumen 356 extends from the proximal end 350 to the distal end 352 and is sized to receive the elongate member 312. The tubular member 314 includes a passive marker 358 on its distal end 352 that allows for visualization of the tubular member 314 in a magnetic resonance image and for device conspicuity without obscuring target tissue during treatment (e.g., biopsy, removal). In an alternative embodiment, a wire member disposed through the tubular member 314 and attached to the distal end 334 if the plurality of cutting members 326 can manipulate the shape of the plurality of cutting members 326 by applying and releasing tension on the wire member. For example, applying tension to the wire member can change the shape of the plurality of cutting members from oblong to circular, allowing for different treatment to be performed by the treatment device 310 and changing the volume of tissue sampled or excised by the treatment device.

In the first, unexpanded configuration, the distal end 322 of the elongate member 312 is disposed within the lumen 356 defined by the tubular member 314. To move the elongate member 312 from the first, unexpanded configuration to the second, expanded configuration a distally-directed force is applied on the elongate member 312 while maintaining the position of the tubular member 314 such that the elongate member 312 is advanced out of the tubular member 314. Alternatively, the position of the elongate member 312 can be maintained while applying a proximally-directed force on the tubular member 314, or a distally-directed force can be applied on the elongate member 312 while applying a proximally-directed force on the tubular member 314. This results in the distal end 322 of the elongate member 312 being advanced out of the tubular member 314 and each cutting member of the plurality of cutting members 326 defining the predefined curve 338. Force can be applied on the elongate member 312 and/or tubular member 314, as described above, until a desired amount of the plurality of cutting members 326 is advanced out of the tubular member 314. Subsequently, torque is applied on the elongate member 312 such that it rotates relative to tissue being treated and the plurality of cutting members 326 cuts the tissue.

Once a desired treatment has been accomplished, the elongate member 312 can be moved from the second, expanded configuration to the first, unexpanded configuration. This can be accomplished by applying a proximally-directed force on the elongate member 312 while maintaining the position of the tubular member 314 such that the elongate member 312 is advanced into the lumen 356 of the tubular member 314. Alternatively, the position of the elongate member 312 can be maintained while applying a distally-directed force on the tubular member 314, or a proximally-directed force can be applied on the elongate member 312 while applying a distally-directed force on the tubular member 314. This results in the distal end 322 of the elongate member 312 being advanced into the lumen 356 of the tubular member 314 and each cutting member of the plurality of cutting members 326 defining a substantially straight configuration within the lumen 356 of the tubular member 314. Force can be applied on the elongate member 312 and/or tubular member 314, as described above, until a desired amount of the plurality of tubular members 326 is advanced into the lumen 356 of the tubular member 314.

An elongate tubular member, elongate member, and a tubular member can be formed of any suitable material and selection of a suitable material to form an elongate tubular member, elongate member, and a tubular member can be based on various considerations, including the intended use of an access device or treatment device of which the member is a component. Examples of MRI compatible materials considered suitable to form an elongate tubular member, elongate member, and/or a tubular member include biocompatible materials, materials that can be made biocompatible, metals, electrically insulating materials, electrically non-conducting materials, non-magnetic materials, shape memory alloys, including nickel-titanium alloys such as Nitinol, stainless steel, including Austenitic stainless steel, stainless steel containing Iron, stainless steel including Inconel, 316 stainless steel, cobalt chromium, cobalt chromium alloys, Inconel, titanium, thermoplastics, polymers, PEEK, carbon-filled PEEK, ceramics, the materials described herein, combinations of the described herein, and any other material considered suitable for a particular embodiment. Examples of markers considered suitable to include in an access device and/or treatment device are described in U.S. Patent Application No. 63/135,801, filed on Jan. 11, 2021, which is hereby incorporated by reference in its entirety for the purpose of describing markers considered suitable to include in an access device and/or treatment device. Any marker included in an access device and/or treatment device can visualized using an image obtained by MRI or identified by a unique pattern recognized and transformed into a virtual instrument within a program and displayed on a screen.

Various methods of performing interventional medical treatment under MRI are described herein. While the methods described herein are shown and described as a series of acts, it is to be understood and appreciated that the methods are not limited by the order of acts, as some acts may in accordance with these methods may be omitted, occur in the order shown and/or described, occur in different orders, and/or occur concurrently with other acts described herein.

Figure 9A:
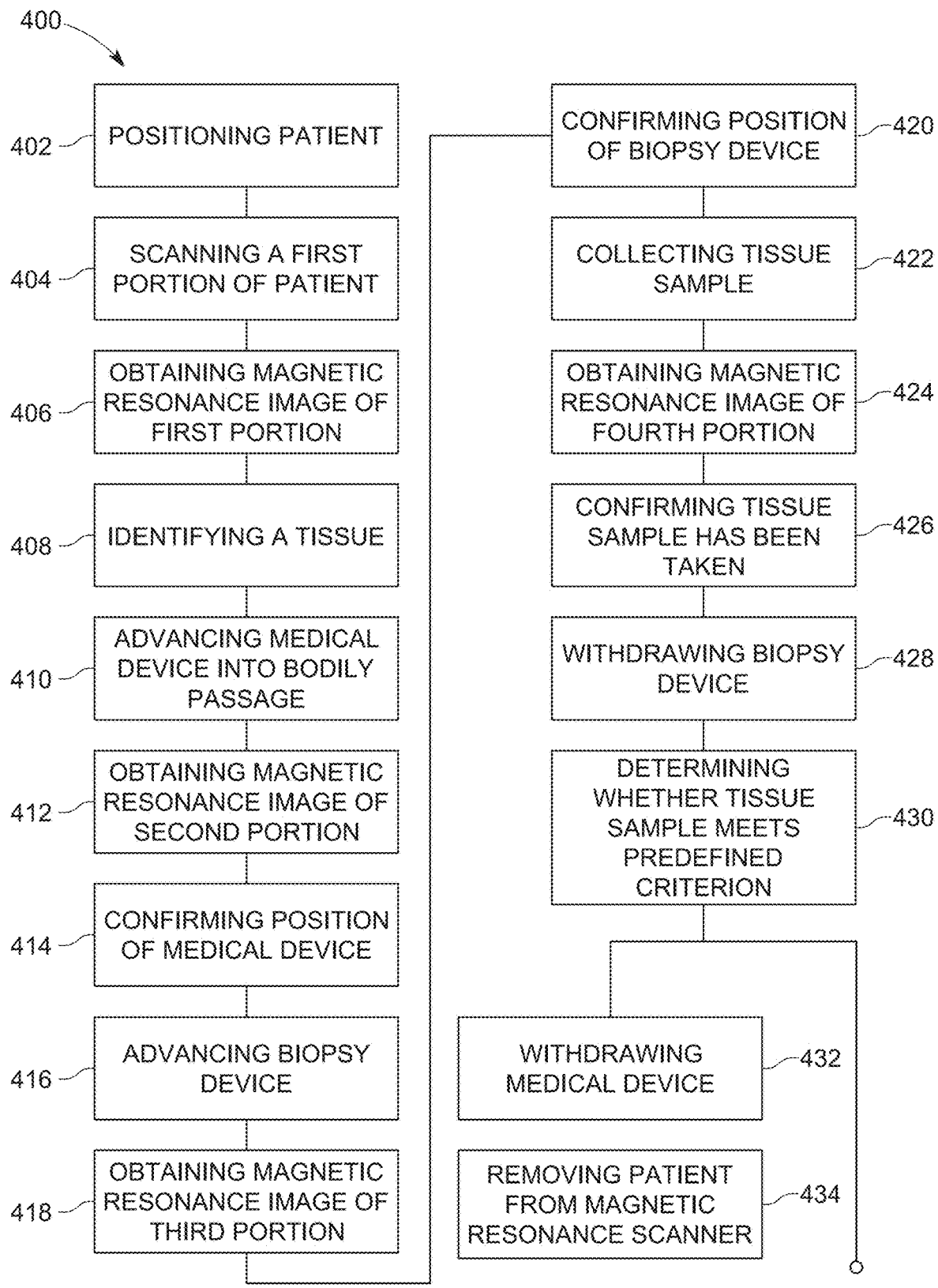
FIGS. 9A and 9B show a schematic illustration of an example method of performing treatment under MRI.
Figure 9B:
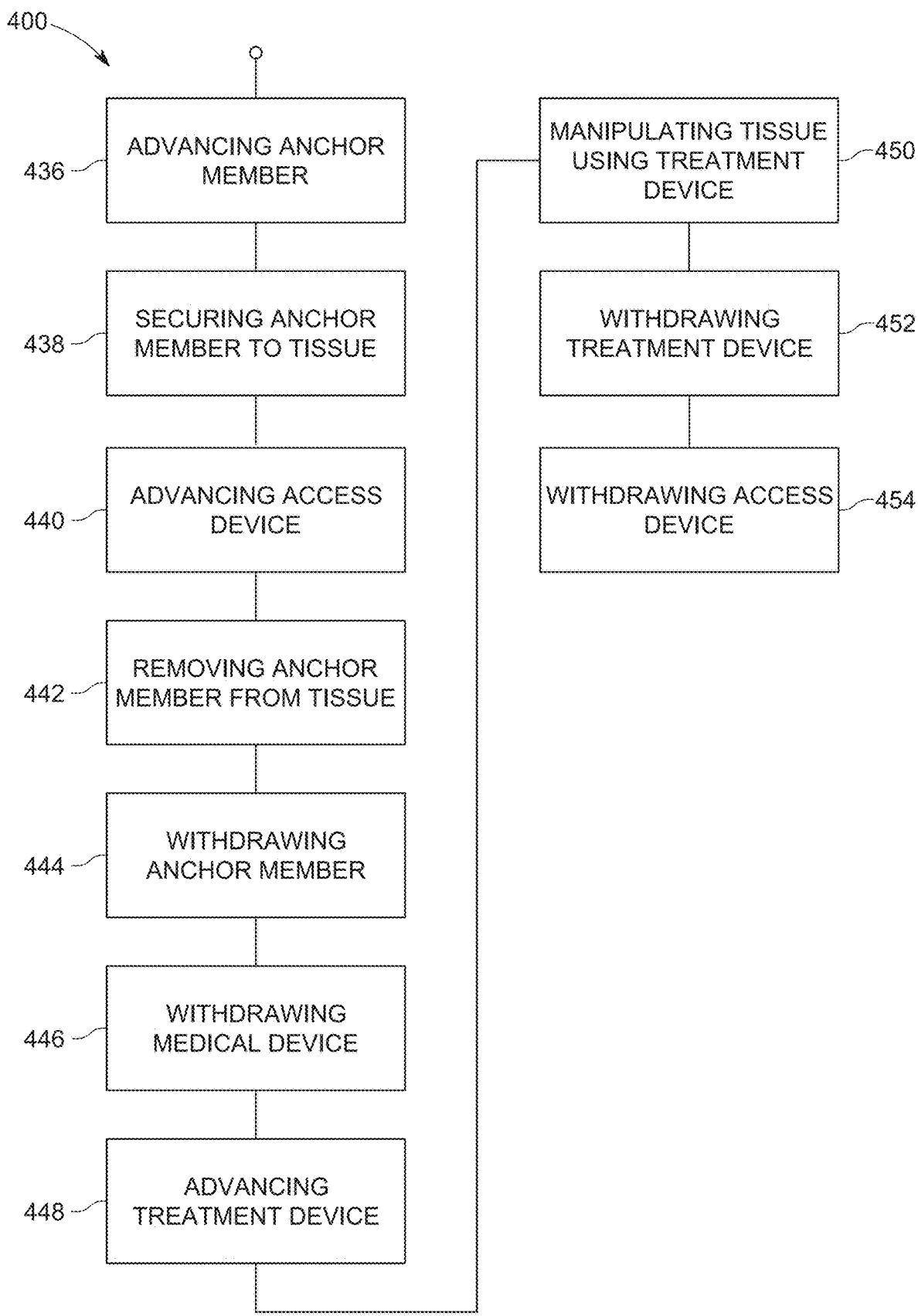

FIGS. 9A and 9B illustrate a schematic illustration of an example method 400 of performing treatment under MRI.

An initial step 402 comprises positioning a patient within a magnetic resonance scanner. Another step 404 comprises scanning a first portion of the patient using the magnetic resonance scanner. Another step 406 comprises obtaining a magnetic resonance image of the first portion of the patient. Another step 408 comprises identifying a tissue that has predefined characteristics using the magnetic resonance image. While the patient remains positioned within the magnetic resonance scanner used to scan a portion of the patient, another step 410 comprises advancing a medical device into a bodily passage and to, within, or adjacent to, the tissue while scanning a second portion of the patient that includes the medical device using the magnetic resonance scanner. Another step 412 comprises obtaining a magnetic resonance image of the second portion of the patient that includes the medical device. Another step 414 comprises confirming the position of the medical device within the bodily passage. Another step 416 comprises advancing a biopsy device through the medical device and to the tissue while scanning a third portion of the patient that includes the biopsy device using the magnetic resonance scanner. Another step 418 comprises obtaining a magnetic resonance image of the third portion of the patient that includes the biopsy device. Another step 420 comprises confirming the position of the biopsy device. Another step 422 comprises collecting a tissue sample from the tissue using the biopsy device while scanning a fourth portion of the patient that includes the biopsy device and the tissue using the magnetic resonance scanner. Another step 424 comprises obtaining a magnetic resonance image of the fourth portion of the patient that includes the biopsy device. Another step 426 comprises confirming the tissue sample has been collected. Another step 428 comprises withdrawing the biopsy device and the tissue sample through the medical device. Another step 430 comprises determining whether the tissue sample meets a predefined criterion. If the tissue sample does not meet the predefined criterion, additional steps comprise 432 withdrawing the medical device from the bodily passage and 434 removing the patient from the magnetic resonance scanner. If the tissue sample meets the predefined criterion, another step 436 comprises advancing an anchor member through the medical device through which the biopsy device was advanced and to the tissue while the patient remains positioned within the magnetic resonance scanner. Another step 438 comprises securing the anchor member to the tissue to retain the position of the medical device relative to the tissue. Another step 440 comprises advancing an access device over the medical device and toward the tissue. Another step 442 comprises removing the anchor member from the tissue. Another step 444 comprises withdrawing the anchor member from the bodily passage. Another step 446 comprises withdrawing the medical device from the bodily passage. Another step 448 comprises advancing a treatment device through the access device and to the tissue. Another step 450 comprises manipulating the tissue using the treatment device. Another step 452 comprises withdrawing the treatment device from the access device. Another step 454 comprises withdrawing the access device from the bodily passage.

Step 402 can be accomplished by positioning a patient within any suitable magnetic resonance scanner, such as conventional magnetic resonance scanners, magnetic resonance scanners that utilize 0.55 T fields, 1.5 T fields, 3 T fields, fields between about 0.055 T and 1.5 T, fields less than 1 T, and any other magnetic resonance scanner considered suitable for a particular embodiment.

Step 404 can be accomplished by scanning any suitable portion of a patient and selection of a suitable portion of a patient to scan can be based on various considerations, including the treatment intended to be performed. Examples of portions of a patient considered suitable to scan include the extremities (e.g., arms, legs), chest, breast, spine, neck, head, abdomen, pelvis, prostate, peri-prostatic structures, tissue surrounding the portions described herein, and/or any other portion of the patient considered suitable for a particular embodiment.

Step 406 can be accomplished by obtaining the magnetic resonance image from the magnetic resonance scanner used in step 402.

Step 408 can be accomplished by reviewing the magnetic resonance image obtained in step 406 and utilizing conventional techniques and/or methods to determine whether tissue has predefined characteristics (e.g., tissue has characteristics indicative of cancer, is a lesion, abnormal mass). Furthermore, the margins (e.g., borders) of any tissue (e.g., abnormal mass, lesions) can be identified and used in further steps, as described herein, to remove and/or treat the tissue.

Step 410 can be accomplished using any suitable medical device, such as the medical devices and/or cannulas described in U.S. Patent Application No. 63/135,801, filed on Jan. 11, 2021, which is hereby incorporated by reference in its entirety for the purpose of describing medical devices considered suitable to complete a step in a method of treatment. FIGS. 16 through 24 illustrate example medical devices 800, 810, 820, 830, 840, 850, 860, 870, and 880 considered suitable to complete a step in a method of treatment. Step 410 can be accomplished by applying a distally-directed force on the medical device such that a distal end of the medical device is advanced into a bodily passage and to, within, or adjacent to, the tissue that has been identified as having the predefined characteristics. A bodily passage can include any suitable portion of a body, including existing bodily passages, bodily lumens, and/or bodily passages created through tissues layers and/or fascia using a device described herein. Step 410 can be accomplished by scanning any suitable portion of a patient and selection of a suitable portion of a patient to scan can be based on various considerations, including the location of the tissue that has predefined characteristics. Examples of portions of a patient considered suitable to scan include portions that include the tissue that has predefined characteristics, portions that include the medical device, portions that include the tissue that has predefined characteristics and the medical device, and any other portion of the patient considered suitable for a particular embodiment. For example, a second portion of the patient can be the same as, or different than, the first portion of the patient.

Step 412 can be accomplished by obtaining the magnetic resonance image from the magnetic resonance scanner used in step 402.

Step 414 can be accomplished by reviewing the magnetic resonance image obtained in step 412 and confirming the medical device is positioned at a desired location within the bodily passage (e.g., at, within, or adjacent to, the tissue that has been identified as having the predefined characteristics). This can be accomplished by visualizing one or more markers included on the medical device. If the medical device is not positioned at a desired location, an optional step comprises manipulating the position of the medical device.

Step 416 can be accomplished by applying a distally-directed force on the biopsy device such that a distal end of the biopsy device is advanced into a lumen defined by the medical device, through the lumen defined by the medical device, and to the tissue that has been identified as having the predefined characteristics. Step 416 can be accomplished by scanning any suitable portion of a patient and selection of a suitable portion of a patient to scan can be based on various considerations, including the location of the tissue that has predefined characteristics. Examples of portions of a patient considered suitable to scan include portions that include the tissue that has predefined characteristics, portions that include the biopsy device, portions that include the tissue that has predefined characteristics and the biopsy device, and any other portion of the patient considered suitable for a particular embodiment. For example, a third portion of the patient can be the same as, or different than, the first portion of the patient and/or the second portion of the patient.

Step 416, step 422, and step 428 can be accomplished using any suitable biopsy device, such as MRI compatible biopsy devices, the Echotip ProCore provided by Cook Medical, the Echotip Ultra provided by Cook Medical, and any other biopsy device considered suitable for a particular embodiment. Alternatively, step 416, step 422, and step 428 can be completed using a biopsy device that is not MRI compatible. This alternative step can comprise advancing the biopsy device through the medical device and to the tissue without scanning a portion of the patient that includes the biopsy device using the magnetic resonance scanner. An alternative to step 422 can comprise collecting a tissue sample using the biopsy device without scanning a portion of the patient that includes the biopsy device and the tissue using the magnetic resonance scanner.

Step 418 can be accomplished by obtaining the magnetic resonance image from the magnetic resonance scanner used in step 402.

Step 420 can be accomplished by reviewing the magnetic resonance image obtained in step 418 and confirming the biopsy device is positioned at a desired location within the bodily passage (e.g., at, within, or adjacent to, the tissue that has been identified as having the predefined characteristics). If the biopsy device is not positioned at a desired location, an optional step comprises manipulating the position of the biopsy device.

Step 422 can be accomplished using the biopsy device and conventional methods of obtaining a tissue sample using a biopsy device. Step 422 can be accomplished by scanning any suitable portion of a patient and selection of a suitable portion of a patient to scan can be based on various considerations, including the location of the tissue that has predefined characteristics. Examples of portions of a patient considered suitable to scan include portions that include the tissue that has predefined characteristics, portions that include the biopsy device, portions that include the tissue that has predefined characteristics and the biopsy device, and any other portion of the patient considered suitable for a particular embodiment. For example, a fourth portion of the patient can be the same as, or different than, the first portion of the patient, the second portion of the patient, and/or the third portion of the patient.

Step 410, step 416, and/or step 422 can optionally be conducted in combination with performing an ultrasound on the portion of the patient that includes the medical device and/or biopsy device. In embodiments in which an ultrasound image is obtained, the magnetic resonance image obtained can be electronically fused with a real-time ultrasound image (e.g., transrectal ultrasound image of a prostate).

Step 424 can be accomplished by obtaining the magnetic resonance image from the magnetic resonance scanner used in step 402.

Step 426 can be accomplished by reviewing the magnetic resonance image obtained in step 424 and confirming the biopsy device has collected the tissue sample (e.g., the tissue that has been identified as having the predefined characteristics). If the biopsy device has not collected the tissue sample, optional steps comprise repeating step 416, step 418, step 420, step 422, step 424, and/or step 426.

Step 406, step 412, step 418, and/or step 424 can comprise obtaining a single still image. Alternatively, step 404, step 410, step 416, and/or step 422 can be repeated any desired number of times such that step 406, step 412, step 418, and/or step 424 comprises obtaining multiple magnetic resonance images of a portion that can be grouped as a cine to show motion.

Step 428 can be accomplished by applying a proximally-directed force on the biopsy device such that it is withdrawn from the lumen defined by the medical device. In an alternative embodiment, step 416, step 418, step 420, step 422, step 424, step 426, and step 428 can be omitted from method 400, and other methods described herein, and the medical device advanced in step 410 can be utilized to obtain a biopsy and steps similar to those described with respect to a biopsy device can be completed utilizing the medical device. In another alternative embodiment, an anchor can be placed, as described herein, the medical device withdrawn, and the anchor used to track a biopsy device to the tissue.

Step 430 can be accomplished using any technique or method considered suitable to determine whether tissue meets predefined criterion. For example, step 430 can utilize conventional techniques and methods for determining whether a tissue sample is malignant, such as frozen section and/or other cytological methods.

Each of step 406, step 408, step 410, step 412, step 414, step 416, step 418, step 420, step 422, step 424, step 426, step 428, and/or step 430 can be accomplished without removing the patient from the magnetic resonance scanner within which the patient is positioned in step 402.

Step 432 can be accomplished by applying a proximally-directed force on the medical device until it is withdrawn from the bodily passage. Step 434 can be accomplished by withdrawing the patient from the magnetic resonance scanner such that the patient is free of the magnetic resonance scanner.

Figure 21:
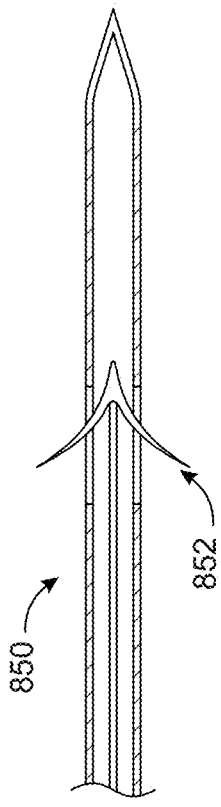
FIG. 21 is a partial sectional view of a sixth example medical device. The barbs of the anchor member are shown disposed through respective passageways of the cannula.
Figure 24:
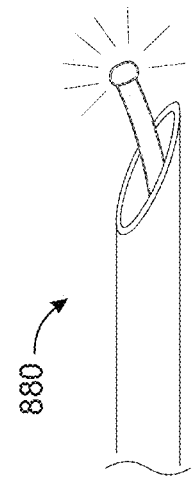
FIG. 24 is a partial perspective view of a ninth example medical device.
Figure 23:
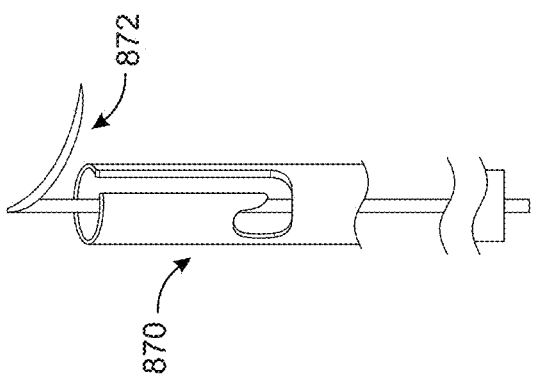
FIG. 23 is a partial elevation view of an eighth example medical device. The barb of the anchor member is shown outside of the lumen defined by the cannula.
Figure 20:
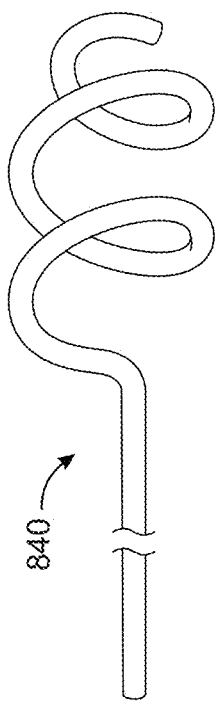
FIG. 20 is a partial elevation view of a fifth example medical device.
Figure 22:
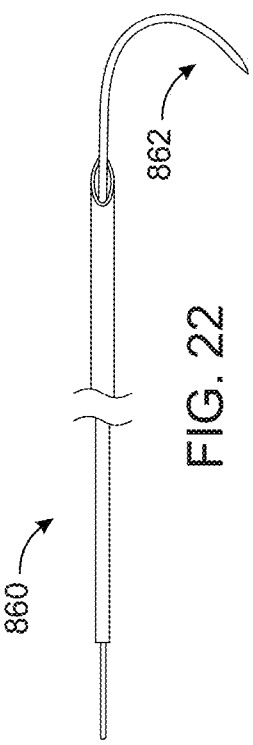
FIG. 22 is a partial top view of a seventh example medical device. A portion of the anchor member is shown free of the cannula.

Step 436 can be accomplished using any suitable anchor member, such as the anchor members described in U.S. Patent Application No. 63/135,801, filed on Jan. 11, 2021, which is hereby incorporated by reference in its entirety for the purpose of describing anchor members considered suitable to complete a step in a method of treatment. FIGS. 21 through 23 illustrate example anchor members 852, 862, and 872 considered suitable to complete a step in a method of treatment. Step 436 can be accomplished by applying a distally-directed force on the anchor member such that a distal end of the anchor member is advanced into a lumen defined by the medical device, through the lumen defined by the medical device, and to the tissue, within, or adjacent to the tissue. Optionally, step 436 can be completed while scanning a fifth portion of the patient that includes the anchor member using the magnetic resonance scanner and additional steps that can be completed subsequent to this optional step include obtaining a magnetic resonance image of the fifth portion of the patient that includes the anchor member, and confirming the position of the anchor member. In embodiments in which it is desired to utilize the magnetic resonance scanner on a second patient that is different from the patient, optional steps that can be completed subsequent to step 438 include removing the patient from the magnetic resonance scanner while maintaining the position of the patient on a surface, positioning a second patient within the magnetic resonance scanner, scanning a portion of the second patient using the magnetic resonance scanner, obtaining a magnetic resonance image of the portion of the second patient, removing the second patient from the magnetic resonance scanner, and repositioning the patient within the magnetic resonance scanner.

Completion of step 438 of securing the anchor member into the tissue will depend on the structural configuration of the anchor member. Examples of suitable actions that can be performed for this step include, but are not limited to, axially advancing the anchoring member through a lumen defined by a medical device until a portion of the anchor member (e.g., barb) becomes disposed within the tissue, or applying torque on the anchoring member until a portion of the anchor member becomes disposed within the tissue. Alternatively, step 438 can comprise anchoring the anchor member into a second, different tissue disposed adjacent to or within the tissue. Step 438 allows for the medical device and/or anchor to be utilized as a guide rail to a target site such that one or more other devices can be advanced over the medical device and/or anchor to a treatment site. Optionally, step 438 can be completed while scanning a sixth portion of the patient that includes the anchor member using the magnetic resonance scanner and additional steps that can be completed subsequent to this optional step include obtaining a magnetic resonance image of the sixth portion of the patient that includes the anchor member, and confirming the position of the anchor member. Step 438 allows for site retention such that the medical device and/or anchor member stays positioned relative to the tissue after biopsy and prior to treatment and can be used to direct a treatment device to the tissue, as described in more detail herein.

Step 440 can be accomplished by applying a distally-directed force on the access device such that a distal end of the access device is advanced over the medical device and to the tissue. Any suitable access device, such as access device 10, can be used to complete step 440. Utilization of access device 10 provides a mechanism for dilating a bodily passage subsequent to advancement of the access device 10 to a point of treatment, as described in more detail herein, which can prevent trauma to critical structures by dilating the bodily passage without cutting or tearing. Optionally, step 440 can be completed while scanning a seventh portion of the patient that includes the access device using the magnetic resonance scanner and additional steps that can be completed subsequent to this optional step include obtaining a magnetic resonance image of the seventh portion of the patient that includes the access device, and confirming the position of the access device (e.g., by visualizing the markers disposed on the access device).

While an access device has been used in step 440, an alternative method can substitute the following steps for step 440 to accomplish sequential dilation of a bodily passage: applying a distally-directed force on a first inner sheath such that a distal end of the first inner sheath is advanced over the medical device and to the tissue; applying a distally-directed force on a second inner sheath such that a distal end of the second inner sheath is advanced over the first inner sheath and to the tissue; and applying a distally-directed force on an outer sheath such that a distal end of the outer sheath is advanced over the second inner sheath and to the tissue.

Completion of step 442 of removing the anchor member from the tissue will depend on the structural configuration of the anchor member. Examples of suitable actions that can be performed for this step include, but are not limited to, applying a proximally-directed force on the anchor member such that it is withdrawn through the lumen defined by a medical device until a portion of the anchor member (e.g., barb) becomes free of the tissue, applying torque to the anchoring member until the portion of the anchor member disposed within the tissue becomes free of the tissue, or applying a distally-directed force on the anchor member such that it is advanced within the lumen defined by a medical device until a portion of the anchor member (e.g., barb) becomes free of the tissue. Alternatively, step 442 can comprise removing the anchor member from a tissue disposed adjacent to or within the tissue. Optionally, step 442 can be completed while scanning a portion of the patient that includes the anchor member using the magnetic resonance scanner and additional steps that can be completed subsequent to this optional step include obtaining a magnetic resonance image of the portion of the patient that includes the anchor member, and confirming the position of the anchor member.

Step 444 can be accomplished by applying a proximally-directed force on the anchor member such that it is withdrawn from the lumen defined by the medical device. In an alternative embodiment, step 436, step 438, step 442, and step 444 can be omitted from method 400 and similar steps can be omitted from other methods described herein.

Step 446 can be accomplished by applying a proximally-directed force on the medical device until it is withdrawn from the bodily passage. Optional steps that can be completed in embodiments in which sequential dilation has been accomplished include withdrawing the first inner sheath and withdrawing the second inner sheath.

In an alternative embodiment, step 440 can comprise withdrawing the medical device from the bodily passage, step 442 can comprise advancing an access device over the anchor member and toward the tissue, step 444 can comprise removing the anchor member from the tissue, and step 446 can comprise withdrawing the anchor member from the bodily passage. In this alternative embodiment, the access device is advanced over the anchor member rather than the medical device. Sequential dilation can also be accomplished over the anchor member and be completed as described herein.

Step 448 can be accomplished by applying a distally-directed force on the treatment device such that a distal end of the treatment device is advanced into a lumen defined by the access device, or in alternative embodiments the outer sheath or dilator, and through the lumen defined by the access device, or in alternative embodiments the outer sheath or dilator, and to the tissue. In embodiments in which the portion of the treatment device that is advanced into the access device has an outside diameter that is greater than the inside diameter of the access device, this step results in dilation of the bodily passage as a result of the access device expanding in response to advancement of the treatment device through the lumen defined by the access device. Any suitable treatment device can be utilized in method 400 and selection of a suitable treatment device can be based on various considerations, such as the intended use of the treatment device. Examples of treatment devices considered suitable to treat tissue for which a tissue sample meets a predefined criterion include treatment device 110, treatment device 210, treatment device 310, dissection tools, optical fibers, optical fibers formed of a material selected from the group consisting of argon, dye, erbium, excimer, Nd:YAG, and $CO^2$, optical fibers that include control cables (e.g., ultra-high molecular weight polyethylene, Dyneema) to direct the fibers toward tissue intended to be treated, needles, cannulas, such as those described herein or incorporated by reference, and any other treatment device considered suitable for a particular embodiment. Optionally, step 448 can be completed while scanning a portion of the patient that includes the treatment device using the magnetic resonance scanner and additional steps that can be completed subsequent to this optional step include obtaining a magnetic resonance image of the portion of the patient that includes the treatment device, and confirming the position of the treatment device.

Step 450 can be accomplished by physically manipulating the tissue using the treatment device, which can include removing of all or a portion of the tissue, introducing a material into the tissue, applying a treatment to the tissue, and performing any other suitable treatment on the tissue. Examples of treatments considered suitable include laser direct therapy, photodynamic therapy (PDT), chemotherapy, a focal treatment, a radical prostatectomy, infusion of ablative agents, such as acetic acid, ethanol, sclerosants (e.g., sodium tetradecyl sulfate), chemotherapeutic agents, and any other treatment considered suitable for a particular embodiment. Optionally, step 450 can be completed while scanning a portion of the patient that includes the treatment device using the magnetic resonance scanner and additional steps that can be completed subsequent to this optional step include obtaining a magnetic resonance image of the portion of the patient that includes the treatment device, and confirming the position of the treatment device. For example, a magnetic resonance scanner can be utilized to determine areas of tissue that become devitalized during ablative therapies. The heating and devitalization of tissue can be monitored such that it occurs in real time and can be used to guide the targeted treatment of the tissue (e.g., prostate).

In embodiments in which treatment device 110 is being utilized to complete step 450, the following steps can be completed to manipulate the tissue: moving the elongate member from the first, unexpanded configuration to the second, expanded configuration; introducing a fluid through each tubular member of the plurality of tubular members; moving the elongate member from the second, expanded configuration to the first, unexpanded configuration. An optional step comprises confirming placement of the treatment device by visualizing the markers via a magnetic resonance image that can be obtained as described herein. These steps can be accomplished as described herein with respect to treatment device 110. Use of treatment device 110 provides a mechanism for controlling the advancement of the plurality of tubular members into the tissue and, therefore, the location of the treatment performed. For example, in embodiments in which agents are introduced through the plurality of tubular members, the tissue can be devitalized and the progression of the treatment monitored by MRI (e.g., by scanning the portion of the tissue that includes the treatment device and reviewing the image obtained from the scan).

In embodiments in which treatment device 210 is being utilized to complete step 450, the following steps can be completed to manipulate the tissue: advancing the elongate member out of the lumen defined by the tubular member; applying tension on the cutting member such that elongate member moves from the first, substantially straight configuration to the second, curved configuration; applying torque on the elongate member such that it rotates relative to the tissue and the cutting blade cuts the tissue; releasing tension from cutting member such that the elongate member moves from the second, curved configuration to the first substantially straight configuration; advancing the elongate member into the lumen defined by the tubular member. An optional step comprises confirming placement of the treatment device by visualizing the markers via a magnetic resonance image that can be obtained as described herein. These steps can be accomplished as described herein with respect to treatment device 210. Use of treatment device 210 provides a mechanism for cutting tissue by rotating the elongate member relative to the tissue as tension is applied to the cutting member and the degree of the curve defined by the elongate member can be manipulated by adjusting the tension applied to the cutting member.

In embodiments in which treatment device 310 is being utilized to complete step 450, the following steps can be completed to manipulate the tissue: moving the elongate member from the first, unexpanded configuration to the second, expanded configuration; applying torque to the elongate member such that it rotates relative to the tissue and the plurality of cutting members cuts the tissue; moving the elongate member from the second, expanded configuration to the first, unexpanded configuration. An optional step comprises confirming placement of the treatment device by visualizing the markers via a magnetic resonance image that can be obtained as described herein. These steps can be accomplished as described herein with respect to treatment device 310. Use of treatment device 310 provides a mechanism for cutting tissue by rotating the elongate member relative to the tissue and for retrieving the cut tissue using the plurality of cutting members as a retrieval basket.

Optionally, step 450 can be repeated. For example, as the space within the body enlarges as step 450 is being completed, more of the treatment device can be introduced into the space created in initial step 450 to increase the area of disruption. Once the space has been maximally enlarged, the treatment device and access device are removed and can then be inserted into different locations of the tissue until the entire tissue that has predefined characteristics is removed.

Step 452 can be accomplished by applying a proximally-directed force on the treatment device until it is withdrawn from the lumen defined by the access device, or in alternative embodiments, the outer sheath or dilator.

Optional steps that can be completed prior, or subsequent, to step 450 or step 452 include applying suction to the access device or treatment device; introducing a flushing fluid through access device or treatment device; introducing a second treatment device (e.g., basket, grasper) through access device and to tissue; manipulating the tissue (e.g., removing, macerating, disrupting using laser, electrosurgical, thermal, or other disruption or ablative methods) using second treatment device; and withdrawing second treatment device.

Step 454 can be accomplished by applying a proximally-directed force on the access device, or in alternative embodiments the outer sheath or dilator, until it is withdrawn from the bodily passage.

Figure 10A:
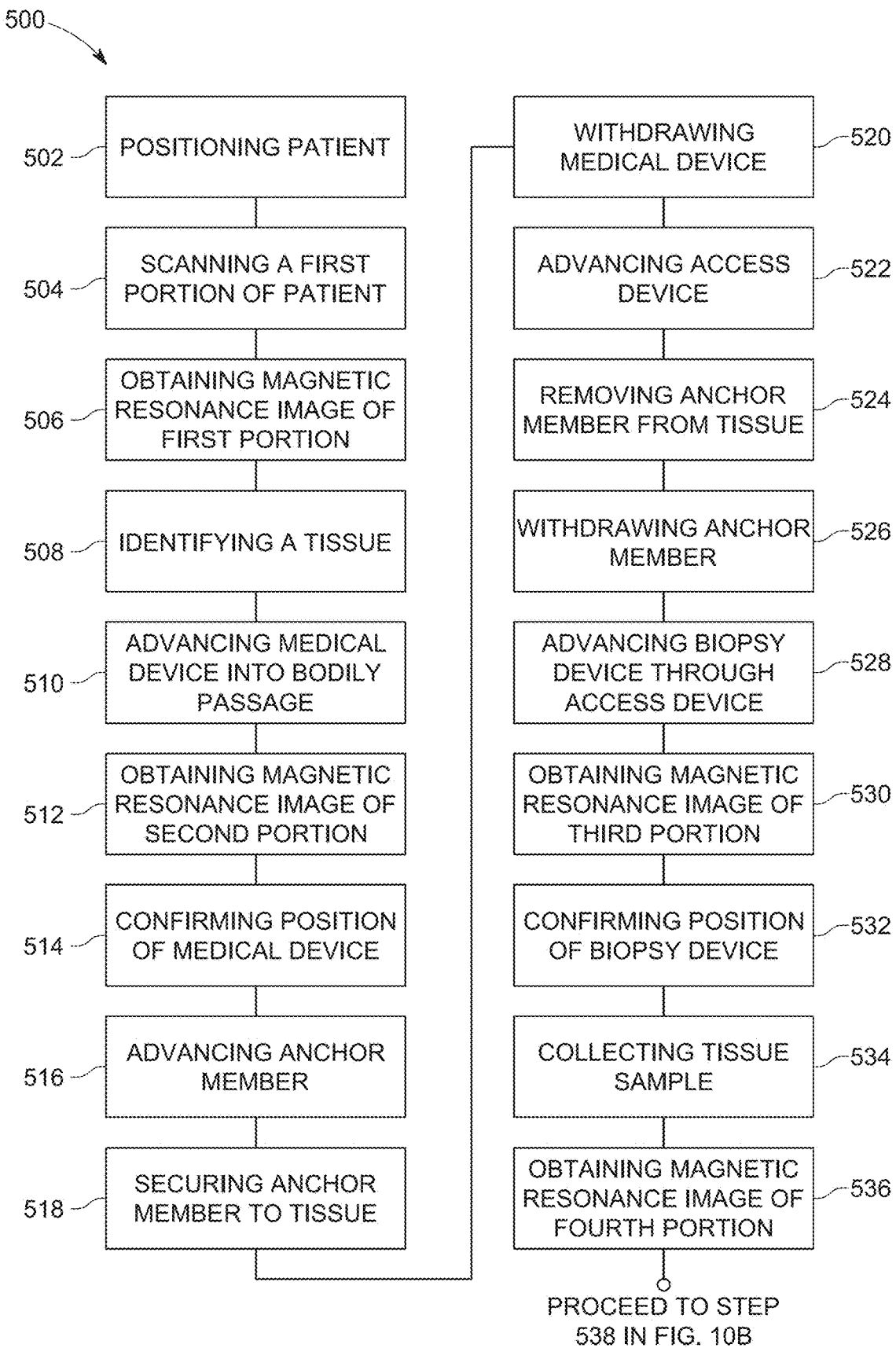
FIGS. 10A and 10B show another schematic illustration of an example method of performing treatment under MRI.
Figure 10B:
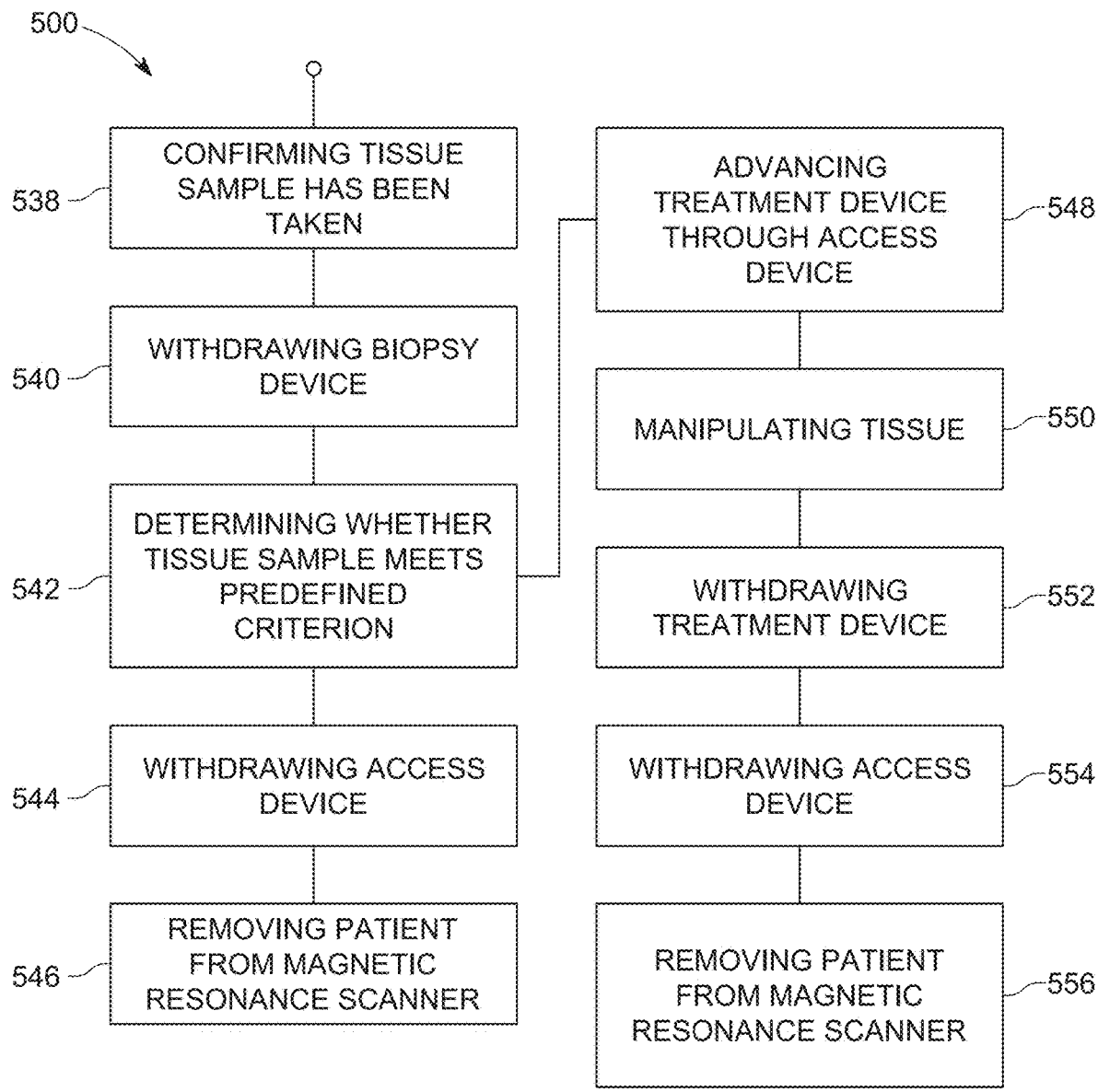

FIGS. 10A and 10B illustrate another schematic illustration of an example method 500 of performing treatment under MRI.

An initial step 502 comprises positioning a patient within a magnetic resonance scanner. Another step 504 comprises scanning a first portion of the patient using the magnetic resonance scanner. Another step 506 comprises obtaining a magnetic resonance image of the first portion of the patient. Another step 508 comprises identifying a tissue that has predefined characteristics using the magnetic resonance image. While the patient remains positioned within the magnetic resonance scanner used to scan a portion of the patient, another step 510 comprises advancing a medical device into a bodily passage and to, within, or adjacent to, the tissue while scanning a second portion of the patient that includes the medical device using the magnetic resonance scanner. Another step 512 comprises obtaining a magnetic resonance image of the second portion of the patient that includes the medical device. Another step 514 comprises confirming the position of the medical device within the bodily passage. Another step 516 comprises advancing an anchor member through the medical device and to the tissue while the patient remains positioned within the magnetic resonance scanner. Another step 518 comprises securing the anchor member to the tissue to retain the position of the anchor member relative to the tissue. Another step 520 comprises withdrawing the medical device from the bodily passage. Another step 522 comprises advancing an access device over the anchor member and toward the tissue. Another step 524 comprises removing the anchor member from the tissue. Another step 526 comprises withdrawing the anchor member from the bodily passage. Another step 528 comprises advancing a biopsy device through the access device and to the tissue while scanning a third portion of the patient that includes the biopsy device using the magnetic resonance scanner. Another step 530 comprises obtaining a magnetic resonance image of the third portion of the patient that includes the biopsy device. Another step 532 comprises confirming the position of the biopsy device. Another step 534 comprises collecting a tissue sample from the tissue using the biopsy device while scanning a fourth portion of the patient that includes the biopsy device and the tissue using the magnetic resonance scanner. Another step 536 comprises obtaining a magnetic resonance image of the fourth portion of the patient that includes the biopsy device. Another step 538 comprises confirming the tissue sample has been collected. Another step 540 comprises withdrawing the biopsy device and the tissue sample through the access device. Another step 542 comprises determining whether the tissue sample meets a predefined criterion. If the tissue sample does not meet the predefined criterion, additional steps comprise 544 withdrawing the outer sheath from the bodily passage and 546 removing the patient from the magnetic resonance scanner. If the tissue sample meets the predefined criterion, another step 548 comprises advancing a treatment device through the access device and to the tissue. Another step 550 comprises manipulating the tissue using the treatment device. Another step 552 comprises withdrawing the treatment device from the access device. Another step 554 comprises withdrawing the access device from the bodily passage. Another step 556 comprises removing the patient from the magnetic resonance scanner.

Figure 11A:
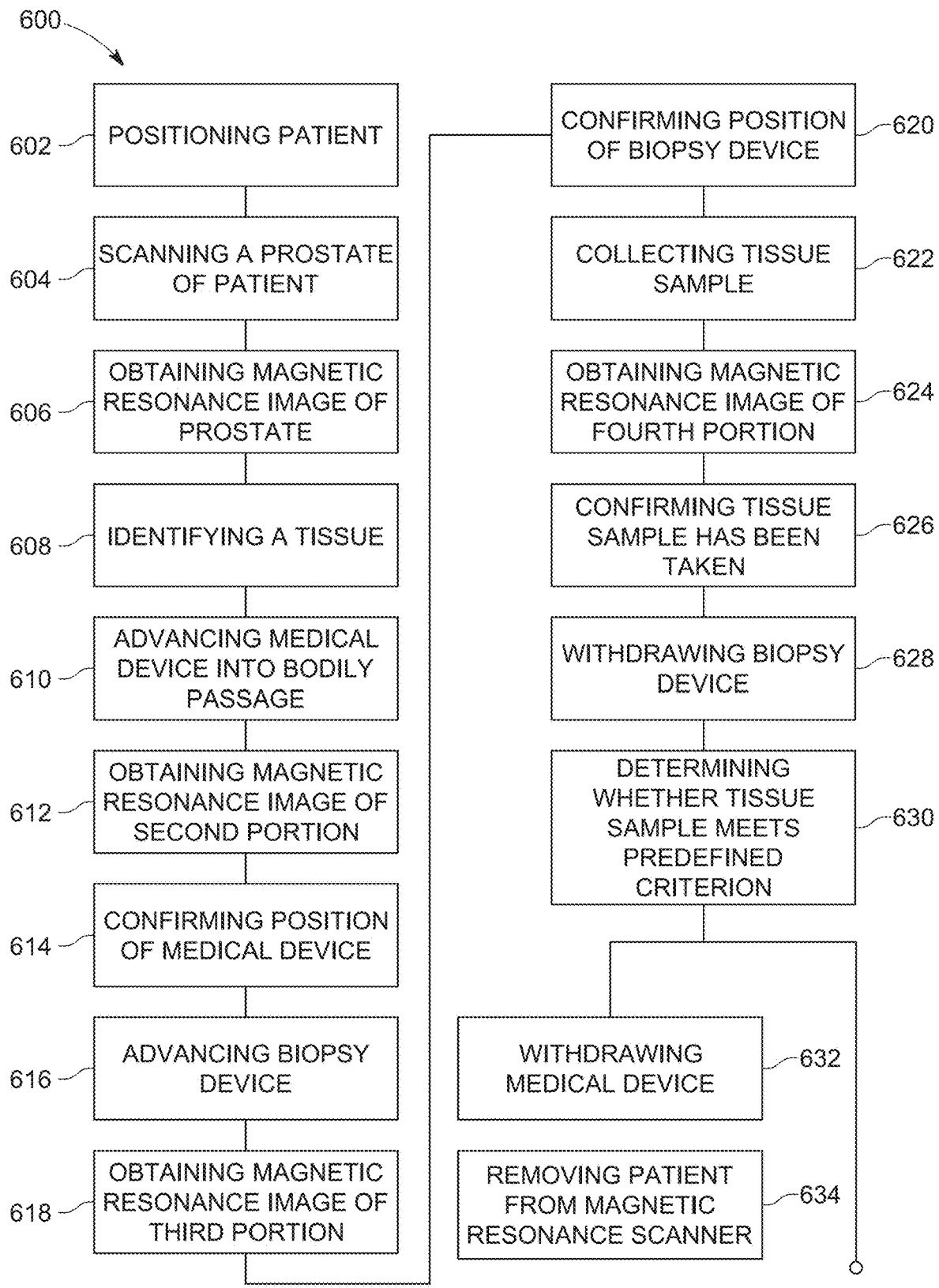
FIGS. 11A and 11B show another schematic illustration of an example method of performing treatment under MRI.
Figure 11B:
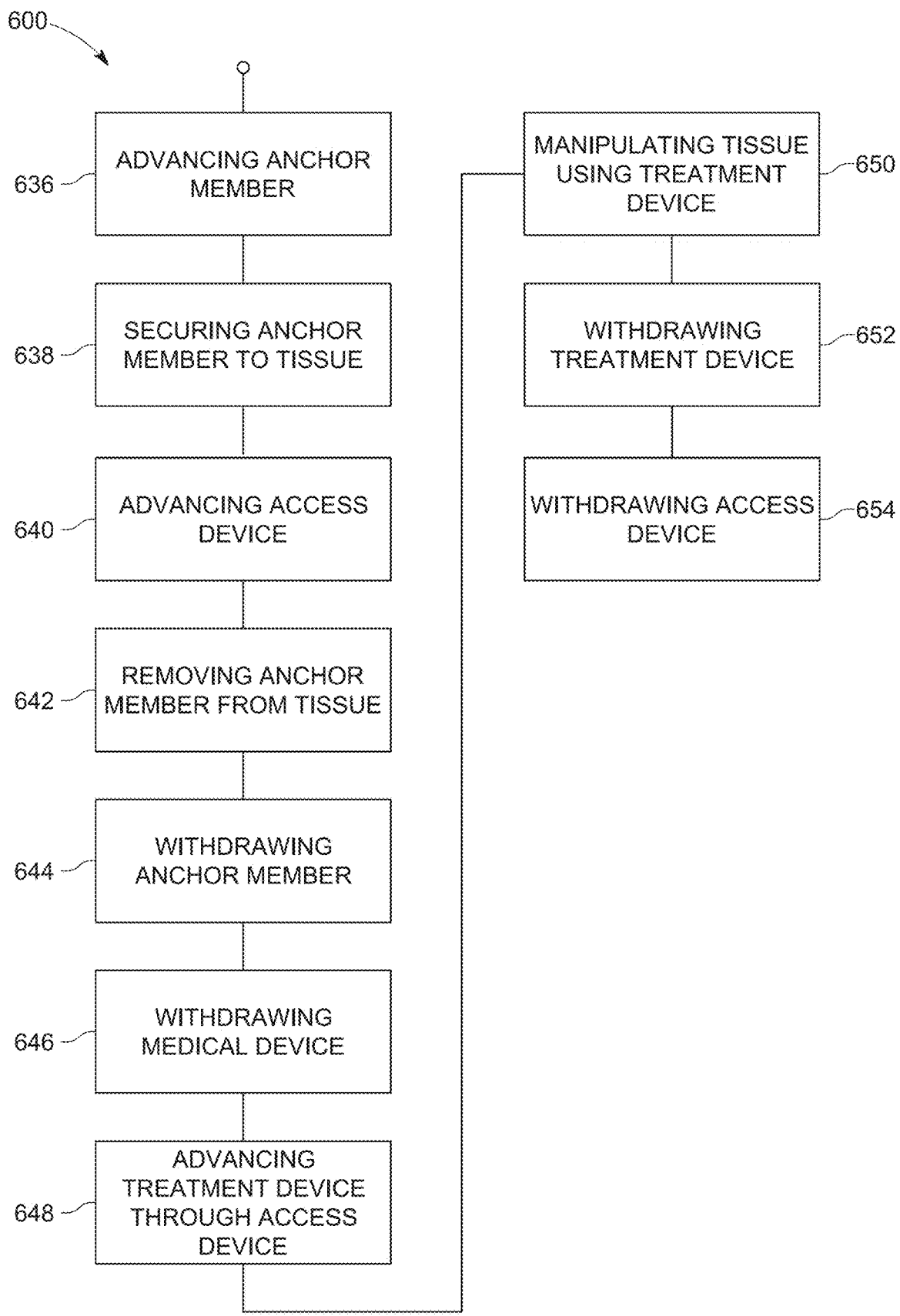

FIGS. 11A and 11B illustrate another schematic illustration of an example method 600 of performing treatment on a prostate under MRI.

An initial step 602 comprises positioning a patient within a magnetic resonance scanner. Another step 604 comprises scanning a prostate and surrounding tissue of the patient using the magnetic resonance scanner. Another step 606 comprises obtaining a magnetic resonance image of the prostate and surrounding tissue of the patient. Another step 608 comprises identifying a tissue within the magnetic resonance image that has predefined characteristics. While the patient remains positioned within the magnetic resonance scanner used to scan the prostate and surrounding tissue, another step 610 comprises advancing a medical device into a bodily passage and to the tissue while scanning a first portion of the patient that includes the medical device using the magnetic resonance scanner. Another step 612 comprises obtaining a magnetic resonance image of the second portion of the patient that includes the medical device. Another step 614 comprises confirming the position of the medical device within the bodily passage. Another step 616 comprises advancing a biopsy device through the medical device and to the tissue while scanning a third portion of the patient that includes the biopsy device using the magnetic resonance scanner. Another step 618 comprises obtaining a magnetic resonance image of the third portion of the patient that includes the biopsy device. Another step 620 comprises confirming the position of the biopsy device. Another step 622 comprises collecting a tissue sample from the tissue using the biopsy device while scanning a fourth portion of the patient that includes the biopsy device and the tissue using the magnetic resonance scanner. Another step 624 comprises obtaining a magnetic resonance image of the fourth portion of the patient that includes the biopsy device. Another step 626 comprises confirming the tissue sample has been collected. Another step 628 comprises withdrawing the biopsy device and the tissue sample through the medical device. Another step 630 comprises determining whether the tissue sample meets a predefined criterion. If the tissue sample does not meet the predefined criterion, additional steps comprise 632 withdrawing the medical device from the bodily passage and 634 removing the patient from the magnetic resonance scanner. If the tissue sample meets the predefined criterion, another step 636 comprises advancing an anchor member through the medical device through which the biopsy device was advanced and to the tissue while the patient remains positioned within the magnetic resonance scanner. Another step 638 comprises securing the anchor member to the tissue to retain the position of the medical device relative to the tissue. Another step 640 comprises advancing an access device over the medical device and toward the tissue. Another step 642 comprises removing the anchor member from the tissue. Another step 644 comprises withdrawing the anchor member from the bodily passage. Another step 646 comprises withdrawing the medical device from the bodily passage. Another step 648 comprises advancing a treatment device through the access device and to the tissue. Another step 650 comprises manipulating the tissue using the treatment device. Another step 652 comprises withdrawing the treatment device from the access device. Another step 654 comprises withdrawing the access device from the bodily passage.

Method 400, method 500, and method 600 are considered advantageous at least because each step of method 400, method 500, and method 600 can be performed during a single patient visit and using the same magnetic resonance scanner, which increases efficiency and reduces the number of patient visits and procedures performed. This results in a set of procedures in which a physician can visualize, diagnose, and treat a patient in a single patient visit. Furthermore, these methods are considered advantageous at least because they provide methods for removing abnormal tissue (e.g., tumor). For example, MR offers high spatial and temporal resolution in real time that can image tissue (e.g., prostate) and assess it both from a functional aspect as well as morphologically. The methods described herein provide for non-invasive abnormal tissue (e.g., tumor) detection, staging, and consequent direction of biopsy and interventional therapies. They can be used to guide physicians to the desired treatment strategies for an individual patient since the imaging quality of MRI is superior as compared to ultrasound. The higher resolution procedures described herein lead to a better outcome for the patient, faster recovery time, less perioperative pain, and less blood loss as compared to open surgical techniques allowing a patient to return to normal activity in a shorter period of time. While some steps have been described as being completed while scanning a portion of the patient using a magnetic resonance scanner and other steps have not been described as being performed while scanning a portion of the patient using a magnetic resonance scanner, any step described herein can be completed while scanning a portion of a patient using the magnetic resonance scanner, and/or an ultrasound device or without scanning a portion of a patient using a magnetic resonance scanner. In embodiments in which an ultrasound image is obtained, the magnetic resonance image obtained can be electronically fused with a real-time ultrasound image (e.g., transrectal ultrasound image of a prostate). While some steps have been described as being completed while scanning a portion of the patient using a magnetic resonance scanner, this step can be broken into two separate steps such that a subsequent step of scanning a portion of a patient using the magnetic resonance scanner can be accomplished. Furthermore, any step which is completed while scanning a portion of the patient using the magnetic resonance scanner can comprise obtaining a single still image and be repeated any desired number of times to obtain multiple magnetic resonance images that can be grouped as a cine to show motion and/or any step which is completed while scanning a portion of the patient using the magnetic resonance scanner can comprise obtaining a live image, such as being completed under live real-time MRI visualization.

Figure 12:
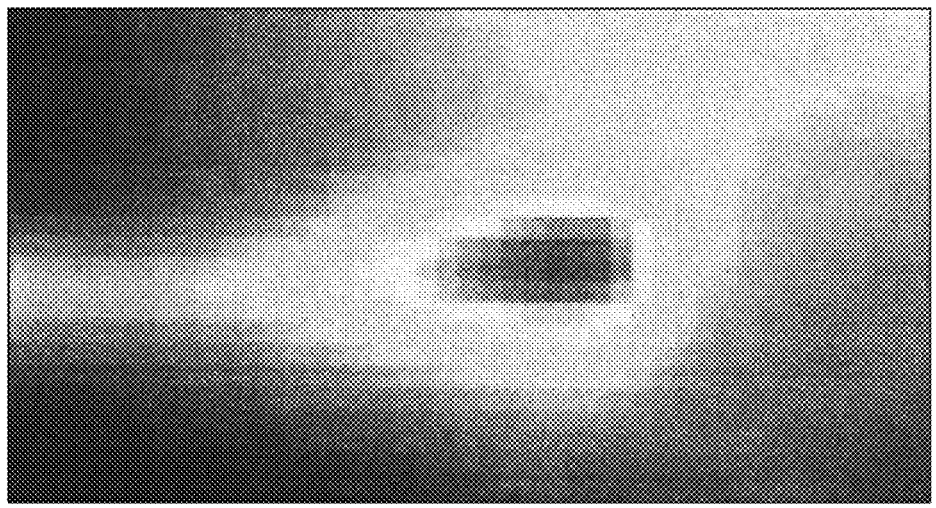
FIG. 12 shows a magnetic resonance thermometry (MRT) proton resonant frequency (PRF) (MRT-PRF) temperature contour around a copper wire.
Figure 13:
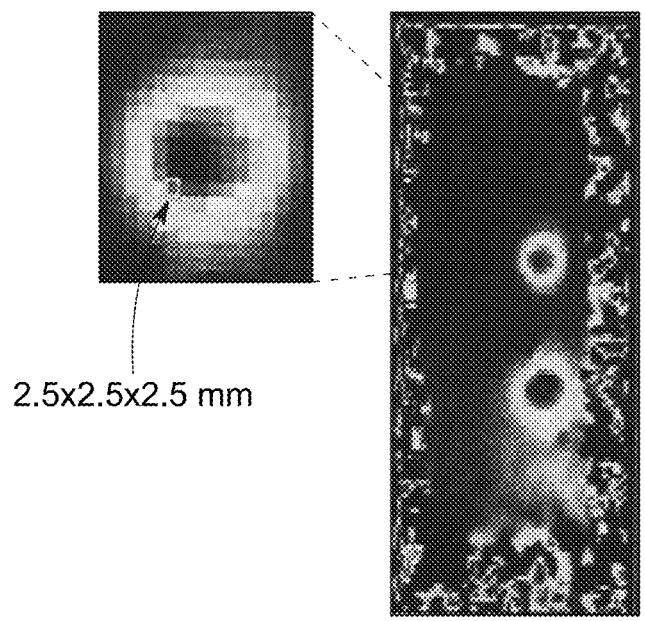
FIG. 13 illustrates a MRT-PRF temperature contour around a stent.
Figure 14:
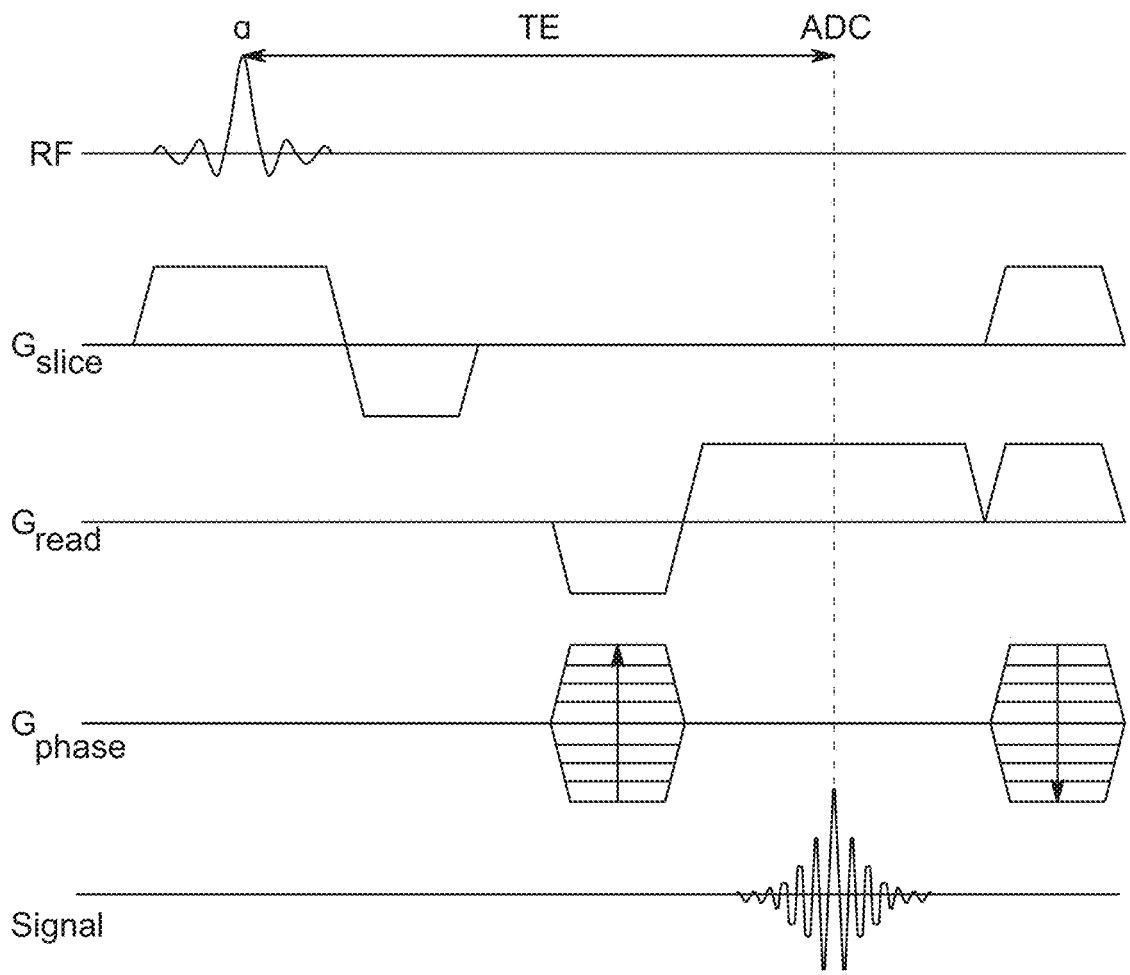
FIG. 14 illustrates a gradient echo pulse sequence used for MRT based on PRF shift method.

Optionally, any step described herein can include concurrently completing magnetic resonance thermometry (MRT) such that noninvasive temperature monitoring using temperature sensitive magnetic resonance (MR) parameters can be accomplished. Alternatively, an optional step, or steps, that can be included in any method described herein can include completing magnetic resonance thermometry (MRT). These optional steps provide a mechanism for monitoring thermal therapies during intraoperative MRI or monitoring temperature near implanted medical device and/or intraoperative devices. In addition, these optional steps provide a mechanism for monitoring a thermal dose during therapy (e.g., monitoring the application of thermally active ablative technologies), monitoring any potential damage from therapy delivery and/or any unintended RF-inducing heating of a device used for the intraoperative MRI procedure, and real-time monitoring of thermal changes within tissue such that feedback control of a thermal dose being delivered to tissue can be completed. Any MRT scanning protocols can be interleaved with any thermal therapy to avoid RF noise or magnetic field perturbations that would negatively impact MR imaging. A thermal therapy can interface with the MRI scanner for automatic thermal dosing based on near real-time MRT. FIG. 12 illustrates an MRT-PRF temperature contour around a copper wire. FIG. 13 illustrates a MRT-PRF temperature contour around a Zilver brand stent. FIG. 14 illustrates a gradient echo pulse sequence used for MRT based on PRF shift method.

While a number of methods have been described herein, it will be appreciated that the method may be a non-invasive method that does not require an invasive intervention by a medical professional. For example, a method may be carried out within a body lumen or passageway, such as the ear canal or a nasal passage, for example in order to place a device within such a passageway. Equally, methods may be implemented on a cadaver or artificial body parts for example for training purposes. Moreover, the skilled person will appreciate that the methods described herein may not be used on the human or animal body at all, but may be used in order to view other types of devices using MRI imaging techniques, for example in an industrial setting.

Figure 15:
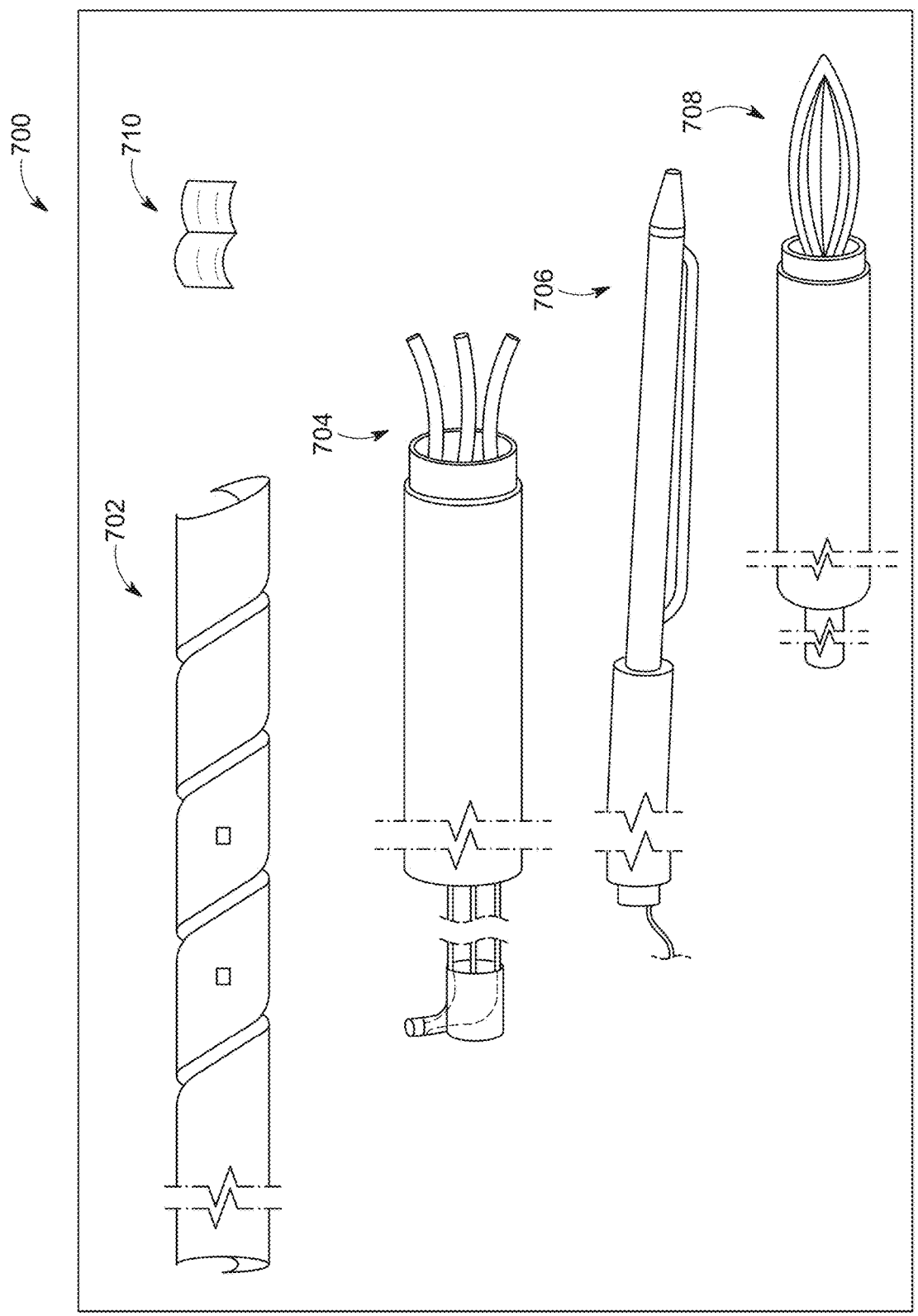
FIG. 15 illustrates an example kit that includes an example access device and example treatment devices.
Figure 17:
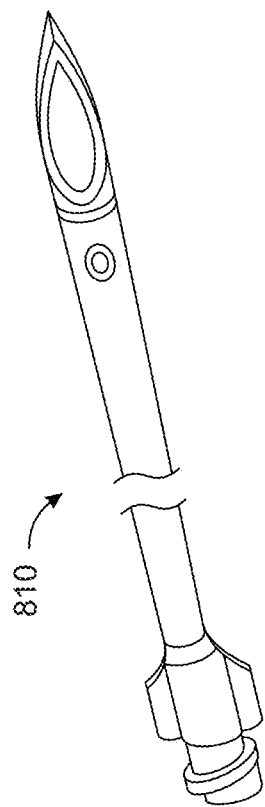
FIG. 17 is a partial perspective view of a second example medical device.
Figure 16:
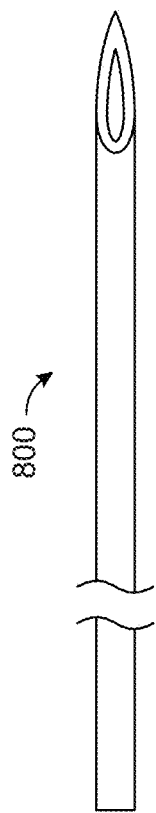
FIG. 16 is a partial elevation view of a first example medical device.
Figure 19:
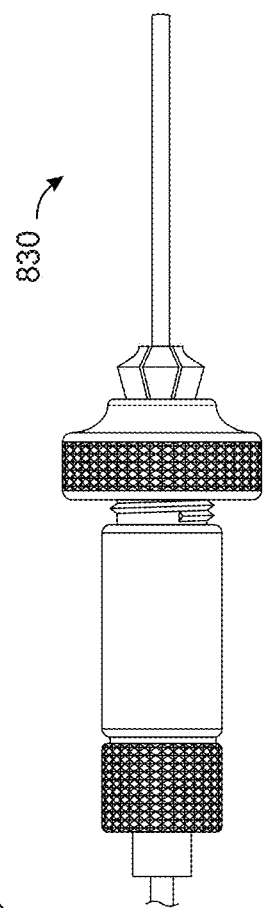
FIG. 19 is a partial elevation view of a fourth example medical device.
Figure 18:
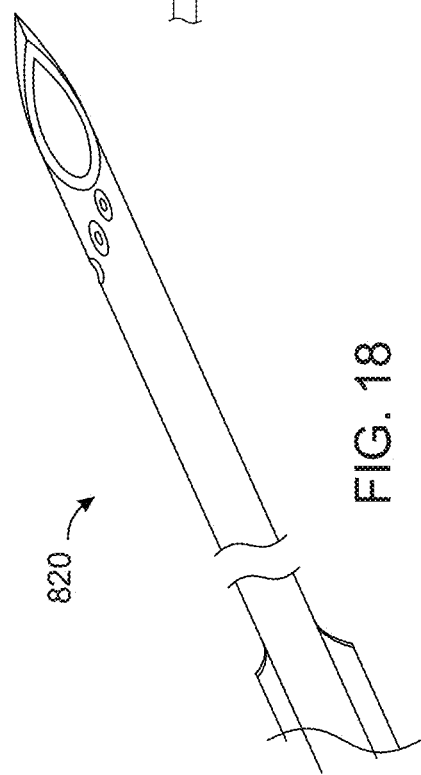
FIG. 18 is a partial perspective view of a third example medical device.

FIG. 15 illustrates an exemplary kit 700 comprising an access device 702 according to an embodiment, such as access device 10 illustrated in FIGS. 1 and 2; a first treatment device 704 according to an embodiment, such as treatment device 110 illustrated in FIGS. 3 and 4; a second treatment device 706 according to an embodiment, such as treatment device 210 illustrated in FIGS. 5 and 6; a third treatment device 708 according to an embodiment, such as treatment device 310 illustrated in FIGS. 7 and 8; and instructions for use 710.

While kit 700 has been illustrated as including one access device 702 and three treatment devices 704, 706, and 708, any suitable number, and type, of access devices and/or treatment devices can be included in a kit. Selection of a suitable number of access devices and/or treatment devices to include in a kit according to a particular embodiment can be based on various considerations, such as the treatment intended to be performed. Examples of numbers of access devices and/or treatment devices considered suitable to include in a kit include at least one, one, two, a plurality, three, four, five, six, seven, eight, nine, ten, more than ten, and any other number considered suitable for a particular embodiment.

Furthermore, while access device 10, treatment device 110, treatment device 210, and treatment device 310, have been illustrated as included in kit 700, any suitable access device and/or treatment device can be included in a kit. Selection of a suitable access device and/or treatment device to include in a kit according to a particular embodiment can be based on various considerations, such as the treatment intended to be performed. Examples of access devices and treatment devices considered suitable to include in a kit include access device 10, treatment device 110, treatment device 210, treatment device 310, and/or any other access device and/or treatment device considered suitable for a particular embodiment.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A method of performing treatment under magnetic resonance imaging comprising:
  positioning a patient within a magnetic resonance scanner;
  scanning a first portion of the patient using the magnetic resonance scanner;
  obtaining a magnetic resonance image of the first portion of the patient;

identifying a tissue that has predefined characteristics using the magnetic resonance image;

while the patient is positioned within the magnetic resonance scanner used to scan the first portion of the patient, advancing a medical device into a bodily passage and to the tissue while scanning a second portion of the patient that includes the medical device using the magnetic resonance scanner;

obtaining a magnetic resonance image of the second portion of the patient that includes the medical device;

confirming the position of the medical device within the bodily passage;

advancing a biopsy device through the medical device and to the tissue while scanning a third portion of the patient that includes the biopsy device using the magnetic resonance scanner;

obtaining a magnetic resonance image of the third portion of the patient that includes the biopsy device;

confirming the position of the biopsy device within the bodily passage;

collecting a tissue sample from the tissue using the biopsy device while scanning a fourth portion of the patient that includes the biopsy device and the tissue using the magnetic resonance scanner;

obtaining a magnetic resonance image of the fourth portion of the patient that includes the biopsy device;

confirming the tissue sample has been collected;

withdrawing the biopsy device and the tissue sample through the medical device;

determining whether the tissue sample meets a predefined criterion;

if the tissue sample meets the predefined criterion, advancing an anchor member through the medical device through which the biopsy device was advanced and to the tissue while the patient remains positioned within the magnetic resonance scanner;

securing the anchor member to the tissue to retain the position of the medical device relative to the tissue;

advancing an access device over the medical device and toward the tissue;

removing the anchor member from the tissue;

withdrawing the anchor member from the bodily passage;

withdrawing the medical device from the bodily passage;

advancing a treatment device through the access device and to the tissue;

manipulating the tissue using the treatment device;

withdrawing the treatment device from the access device;

withdrawing the access device from the bodily passage;

wherein the treatment device comprises:

an elongate member moveable between a first, unexpanded configuration and a second, expanded configuration, the elongate member having a lengthwise axis, a proximal end, a distal end, an adaptor, and a plurality of tubular members attached to the adaptor, the adaptor disposed on the proximal end of the elongate member, having a port, and defining a lumen, each tubular member of the plurality of tubular members having a tubular member proximal end, a tubular member distal end, and a tubular member main body that defines a tubular member lumen and a predefined curve; and a tubular member partially disposed over the elongate member.

2. A method of performing treatment under magnetic resonance imaging comprising:

positioning a patient within a magnetic resonance scanner;

scanning a first portion of the patient using the magnetic resonance scanner;

obtaining a magnetic resonance image of the first portion of the patient;

identifying a tissue that has predefined characteristics using the magnetic resonance image;

while the patient is positioned within the magnetic resonance scanner used to scan the first portion of the patient, advancing a medical device into a bodily passage and to the tissue while scanning a second portion of the patient that includes the medical device using the magnetic resonance scanner;

obtaining a magnetic resonance image of the second portion of the patient that includes the medical device;

confirming the position of the medical device within the bodily passage;

advancing a biopsy device through the medical device and to the tissue while scanning a third portion of the patient that includes the biopsy device using the magnetic resonance scanner;

obtaining a magnetic resonance image of the third portion of the patient that includes the biopsy device;

confirming the position of the biopsy device within the bodily passage;

collecting a tissue sample from the tissue using the biopsy device while scanning a fourth portion of the patient that includes the biopsy device and the tissue using the magnetic resonance scanner;

obtaining a magnetic resonance image of the fourth portion of the patient that includes the biopsy device;

confirming the tissue sample has been collected;

withdrawing the biopsy device and the tissue sample through the medical device;

determining whether the tissue sample meets a predefined criterion;

if the tissue sample meets the predefined criterion, advancing an anchor member through the medical device through which the biopsy device was advanced and to the tissue while the patient remains positioned within the magnetic resonance scanner;

securing the anchor member to the tissue to retain the position of the medical device relative to the tissue;

advancing an access device over the medical device and toward the tissue;

removing the anchor member from the tissue;

withdrawing the anchor member from the bodily passage;

withdrawing the medical device from the bodily passage;

advancing a treatment device through the access device and to the tissue;

manipulating the tissue using the treatment device;

withdrawing the treatment device from the access device;

withdrawing the access device from the bodily passage;

wherein the treatment device comprises:

an elongate member moveable between a first, unexpanded configuration and a second, expanded configuration, the elongate member having a lengthwise axis, a proximal end, a distal end, an adaptor, and a plurality of tubular members attached to the adaptor, the adaptor disposed on the proximal end of the elongate member, having a port, and defining a lumen, each tubular member of the plurality of tubular members having a tubular member proximal end, a tubular member distal end, and a tubular member main body that defines a tubular member lumen and a predefined curve; and a tubular member partially disposed over the elongate member;

wherein each tubular member of the plurality of tubular members is moveable between a substantially straight configuration when the elongate member is in the first, unexpanded configuration and a curved configuration when the elongate member is in the second, expanded configuration.

3. The method of claim 2, further comprising:

moving the elongate member from the first, unexpanded configuration to the second, expanded configuration;

introducing a fluid through each tubular member of the plurality of tubular members; and moving the elongate member from the second, expanded configuration to the first, unexpanded configuration.

4. A method of performing treatment under magnetic resonance imaging comprising:

positioning a patient within a magnetic resonance scanner;

scanning a first portion of the patient using the magnetic resonance scanner;

obtaining a magnetic resonance image of the first portion of the patient;

identifying a tissue that has predefined characteristics using the magnetic resonance image;

while the patient is positioned within the magnetic resonance scanner used to scan the first portion of the patient, advancing a medical device into a bodily passage and to the tissue while scanning a second portion of the patient that includes the medical device using the magnetic resonance scanner;

obtaining a magnetic resonance image of the second portion of the patient that includes the medical device;

confirming the position of the medical device within the bodily passage;

advancing a biopsy device through the medical device and to the tissue while scanning a third portion of the patient that includes the biopsy device using the magnetic resonance scanner;

obtaining a magnetic resonance image of the third portion of the patient that includes the biopsy device;

confirming the position of the biopsy device within the bodily passage;

collecting a tissue sample from the tissue using the biopsy device while scanning a fourth portion of the patient that includes the biopsy device and the tissue using the magnetic resonance scanner;

obtaining a magnetic resonance image of the fourth portion of the patient that includes the biopsy device;

confirming the tissue sample has been collected;

withdrawing the biopsy device and the tissue sample through the medical device;

determining whether the tissue sample meets a predefined criterion;

if the tissue sample meets the predefined criterion, advancing an anchor member through the medical device through which the biopsy device was advanced and to the tissue while the patient remains positioned within the magnetic resonance scanner;

securing the anchor member to the tissue to retain the position of the medical device relative to the tissue;

advancing an access device over the medical device and toward the tissue;

removing the anchor member from the tissue;

withdrawing the anchor member from the bodily passage;

withdrawing the medical device from the bodily passage;

advancing a treatment device through the access device and to the tissue;

manipulating the tissue using the treatment device;

withdrawing the treatment device from the access device;

withdrawing the access device from the bodily passage;

wherein the treatment device comprises:

an elongate member moveable between a first, unexpanded configuration and a second, expanded configuration, the elongate member having a lengthwise axis, a proximal end, a distal end, an adaptor, and a plurality of tubular members attached to the adaptor, the adaptor disposed on the proximal end of the elongate member, having a port, and defining a lumen, each tubular member of the plurality of tubular members having a tubular member proximal end, a tubular member distal end, and a tubular member main body that defines a tubular member lumen and a predefined curve; and a tubular member partially disposed over the elongate member;

wherein the treatment device includes a plurality of markers disposed on the elongate member.

5. The method of claim 1, wherein the access device comprises an elongate tubular member moveable between a first, unexpanded configuration and a second, expanded configuration, the elongate tubular member having a central lengthwise axis, a proximal end, a distal end, an axial length, and a main body that defines a circumferential wall, a lumen, a proximal opening, a distal opening, and a main body opening, the main body opening arranged in a spiral relative to the lengthwise axis and extending circumferentially along the circumferential wall.

6. The method of claim 5, wherein the main body opening extends along the entire axial length of the elongate tubular member from the proximal end to the distal end.

7. The method of claim 5, wherein the access device includes a polymer sleeve disposed over the elongate member.

8. The method of claim 5, wherein the access device includes a plurality of passive markers on the elongate member.

9. The method of claim 1, wherein the treatment device includes one or more markers visible under a magnetic resonance image.

10. The method of claim 2, wherein the access device comprises an elongate tubular member moveable between a first, unexpanded configuration and a second, expanded configuration, the elongate tubular member having a central lengthwise axis, a proximal end, a distal end, an axial length, and a main body that defines a circumferential wall, a lumen, a proximal opening, a distal opening, and a main body opening, the main body opening arranged in a spiral relative to the lengthwise axis and extending circumferentially along the circumferential wall.

11. The method of claim 10, wherein the main body opening extends along the entire axial length of the elongate tubular member from the proximal end to the distal end.

12. The method of claim 10, wherein the access device includes a polymer sleeve disposed over the elongate member.

13. The method of claim 10, wherein the access device includes a plurality of passive markers on the elongate member.

14. The method of claim 2, wherein the treatment device includes one or more markers visible under a magnetic resonance image.

15. The method of claim 4, wherein the access device comprises an elongate tubular member moveable between a first, unexpanded configuration and a second, expanded configuration, the elongate tubular member having a central lengthwise axis, a proximal end, a distal end, an axial length, and a main body that defines a circumferential wall, a lumen, a proximal opening, a distal opening, and a main body opening, the main body opening arranged in a spiral relative to the lengthwise axis and extending circumferentially along the circumferential wall.

16. The method of claim 15, wherein the main body opening extends along the entire axial length of the elongate tubular member from the proximal end to the distal end.

17. The method of claim 15, wherein the access device includes a polymer sleeve disposed over the elongate member.

18. The method of claim 15, wherein the access device includes a plurality of passive markers on the elongate member.

\* \* \* \* \*

UNITED STATES PATENT AND TRADEMARK OFFICE
CERTIFICATE OF CORRECTION

PATENT NO. : 12,201,321 B2  
APPLICATION NO. : 17/573104  
DATED : January 21, 2025  
INVENTOR(S) : Neal Fearnot et al.

Page 1 of 1

It is certified that error appears in the above-identified patent and that said Letters Patent is hereby corrected as shown below:

On the Title Page

Item (12) First Named Inventor, please correct from:
"Gross et al."
To:
--Fearnot et al.--

Item (72) Inventors:, please correct from:
"David Gross, Lafayette, IN (US); Neal Fearnot, West Lafayette, IN (US); Sean D. Chambers, Bloomington, IN (US); Eric Brandner, West Lafayette, IN (US); Ram H. Paul Jr., Bloomington, IN (US); Gary L. Neff, Bloomington, IN (US); Creasy Clauser Huntsman, Lafayette, IN (US)"
To:
--Neal Fearnot, West Lafayette, IN (US); Sean D. Chambers, Bloomington, IN (US); Eric Brandner, West Lafayette, IN (US); Ram H. Paul Jr., Bloomington, IN (US); Gary L. Neff, Bloomington, IN (US); Creasy Clauser Huntsman, Lafayette, IN (US)--

Signed and Sealed this  
Eighteenth Day of March, 2025

Coke Morgan Stewart  
*Acting Director of the United States Patent and Trademark Office*